(12) United States Patent
Stephens et al.

(10) Patent No.: US 12,650,358 B2
(45) Date of Patent: Jun. 9, 2026

(54) METHOD AND SYSTEM FOR DETECTING A STRUCTURAL ANOMALY IN A PIPELINE NETWORK

(71) Applicant: THE UNIVERSITY OF ADELAIDE, Adelaide (AU)

(72) Inventors: Mark Leslie Stephens, Adelaide (AU); Luke Dix, Adelaide (AU); Chi Zhang, Adelaide (AU); Jinzhe Gong, Adelaide (AU); Benjamin Cazzolato, Adelaide (AU); Martin F. Lambert, Adelaide (AU)

(73) Assignee: THE UNIVERSITY OF ADELAIDE, Adelaide (AU)

( * ) Notice: Subject to any disclaimer, the term of this patent is extended or adjusted under 35 U.S.C. 154(b) by 1116 days.

(21) Appl. No.: 17/605,680

(22) PCT Filed: Apr. 24, 2020

(86) PCT No.: PCT/AU2020/000036
§ 371 (c)(1),
(2) Date: Oct. 22, 2021

(87) PCT Pub. No.: WO2020/215117
PCT Pub. Date: Oct. 29, 2020

(65) Prior Publication Data
US 2022/0163420 A1 May 26, 2022

(30) Foreign Application Priority Data

Apr. 24, 2019 (AU) ................................ 2019901400
Apr. 24, 2019 (AU) ................................ 2019901401

(51) Int. Cl.
G01M 3/24 (2006.01)
E03B 7/00 (2006.01)
(Continued)

(52) U.S. Cl.
CPC ............. G01M 3/243 (2013.01); E03B 7/003 (2013.01); E03B 7/02 (2013.01); G01N 29/12 (2013.01);
(Continued)

(58) Field of Classification Search
CPC . E03B 7/003; E03B 7/02; E03B 7/071; F17D 5/06; G01M 3/243; G01M 3/2807;
(Continued)

(56) References Cited

U.S. PATENT DOCUMENTS

2005/0279169 A1* 12/2005 Lander .................. G01N 29/14
73/592
2006/0174707 A1 8/2006 Zhang
(Continued)

FOREIGN PATENT DOCUMENTS

WO WO 2018/051287 3/2018

OTHER PUBLICATIONS

Boll "Suppression of Acoustic Noise in Speech Using Spectral Subtraction," IEEE Transactions on Acoustics, Speech, and Signal Processing, Apr. 1979, vol. ASSP-27, No. 2, pp. 113-120.
(Continued)

*Primary Examiner* — Catherine T. Rastovski
(74) *Attorney, Agent, or Firm* — Sheridan Ross PC

(57) ABSTRACT

A method for detecting a structural anomaly in a pipeline supply network is disclosed where the pipeline supply network is configured to supply fluid to multiple receiving locations. The method comprises receiving acoustic signal data from a selected location in the pipeline supply network and generating a first time window of acoustic signal data based on the acoustic signal data. The method then includes benchmarking the first time window of acoustic signal data with respect to historical background acoustic signal data characterising the pipeline supply network to generate a
(Continued)

corresponding background benchmarked first time window of acoustic signal data and then determining an anomaly measure for the background benchmarked first time window of acoustic signal data where the anomaly measure indicates a presence of the structural anomaly.

23 Claims, 12 Drawing Sheets

(51) Int. Cl.
    *E03B 7/02*           (2006.01)
    *G01N 29/12*        (2006.01)
    *G01N 33/2045*     (2019.01)

(52) U.S. Cl.
    CPC . *G01N 33/2045* (2019.01); *G01N 2291/0234* (2013.01)

(58) Field of Classification Search
    CPC ............. G01M 5/0025; G01M 5/0033; G01M 5/0066; G01N 29/12; G01N 33/2045; G01N 2291/0234; Y02A 20/15; G01H 3/04; G01H 3/10
    See application file for complete search history.

(56)              References Cited

U.S. PATENT DOCUMENTS

| | | |
|---|---|---|
| 2008/0143344 A1 | 6/2008 | Focia et al. |
| 2013/0179095 A1 | 7/2013 | Stevens et al. |
| 2014/0005958 A1 | 1/2014 | Baliga |
| 2014/0165731 A1* | 6/2014 | Linford ................ G01N 29/024 |
| | | 73/592 |
| 2015/0276545 A1 | 10/2015 | Takahashi et al. |
| 2016/0035370 A1 | 2/2016 | Krini et al. |
| 2017/0212003 A1* | 7/2017 | Campan .................. G06F 17/18 |
| 2017/0307466 A1* | 10/2017 | Brennan, Jr. .......... G01F 1/666 |
| 2018/0252611 A1* | 9/2018 | Cole ..................... G01M 3/243 |
| 2019/0137353 A1* | 5/2019 | Cole ..................... H04B 17/23 |

OTHER PUBLICATIONS

Ephraim et al. "Speech Enhancement Using a Minimum Mean-Square Error Short-Time Spectral Amplitude Estimator," IEEE Transactions on Acoustics, Speech, and Signal Processing, Dec. 1984, vol. ASSP-32, No. 6, pp. 1109-1121.
International Search Report and Written Opinion for International (PCT) Patent Application No. PCT/AU2020/000036, dated May 25, 2020, 11 pages.

* cited by examiner

100

110

200

Receive Acoustic Signal Data — 210

Generate First Time Window of Acoustic Signal Data — 220

Benchmark First Time Window Based on Historical Background Acoustic Signal Data to Generate Background Benchmarked First Time Window — 230

Determine Anomaly Measure to Indicate Presence of the Structural Anomaly — 240

Figures 5, 6:
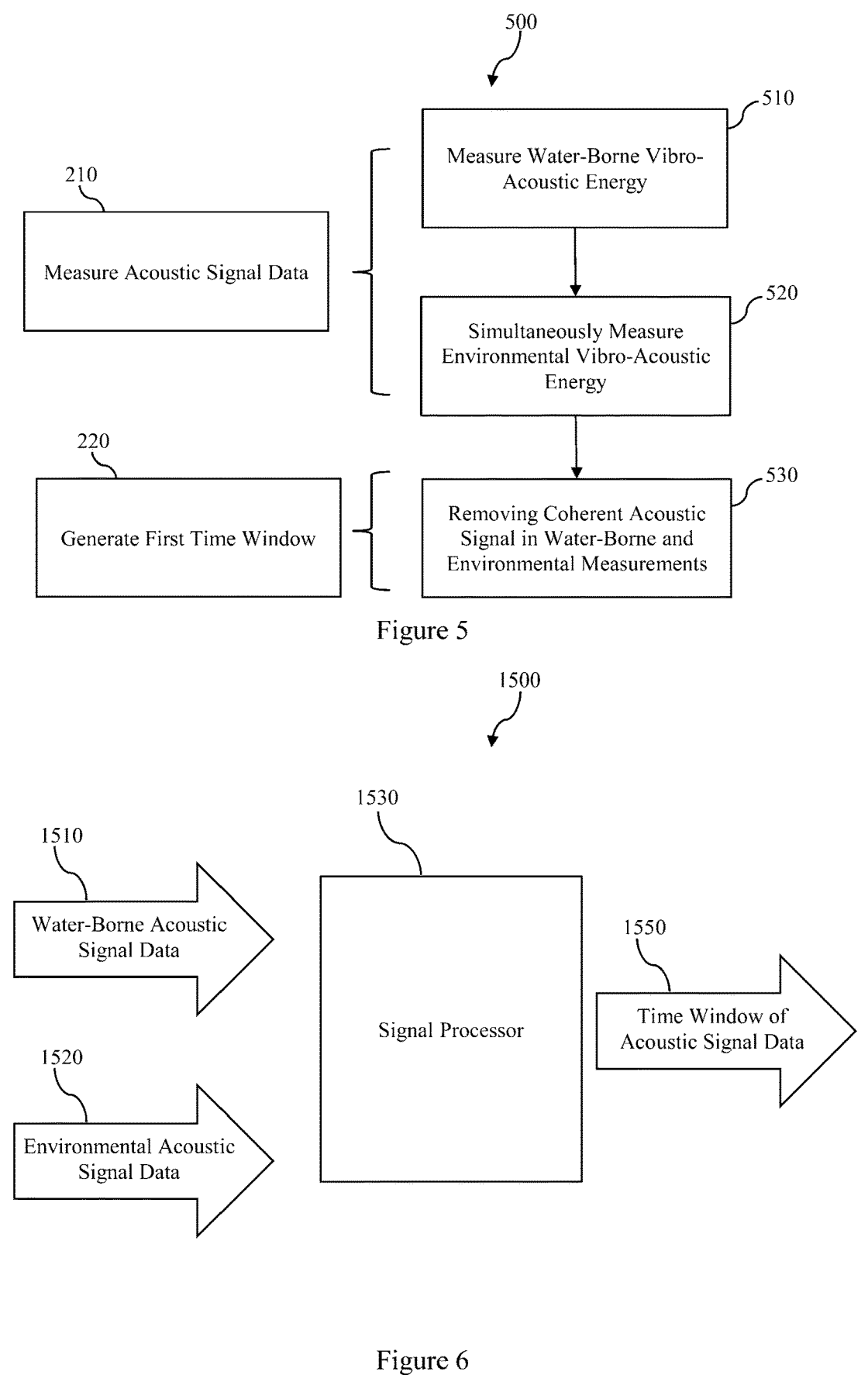

500

510

Measure Water-Borne Vibro-Acoustic Energy

210

Measure Acoustic Signal Data

520

Simultaneously Measure Environmental Vibro-Acoustic Energy

220

Generate First Time Window

530

Removing Coherent Acoustic Signal in Water-Borne and Environmental Measurements

Water-Borne Acoustic Signal Data

Signal Processor

1550

Time Window of Acoustic Signal Data

1520

Environmental Acoustic Signal Data

Figures 10, 11:
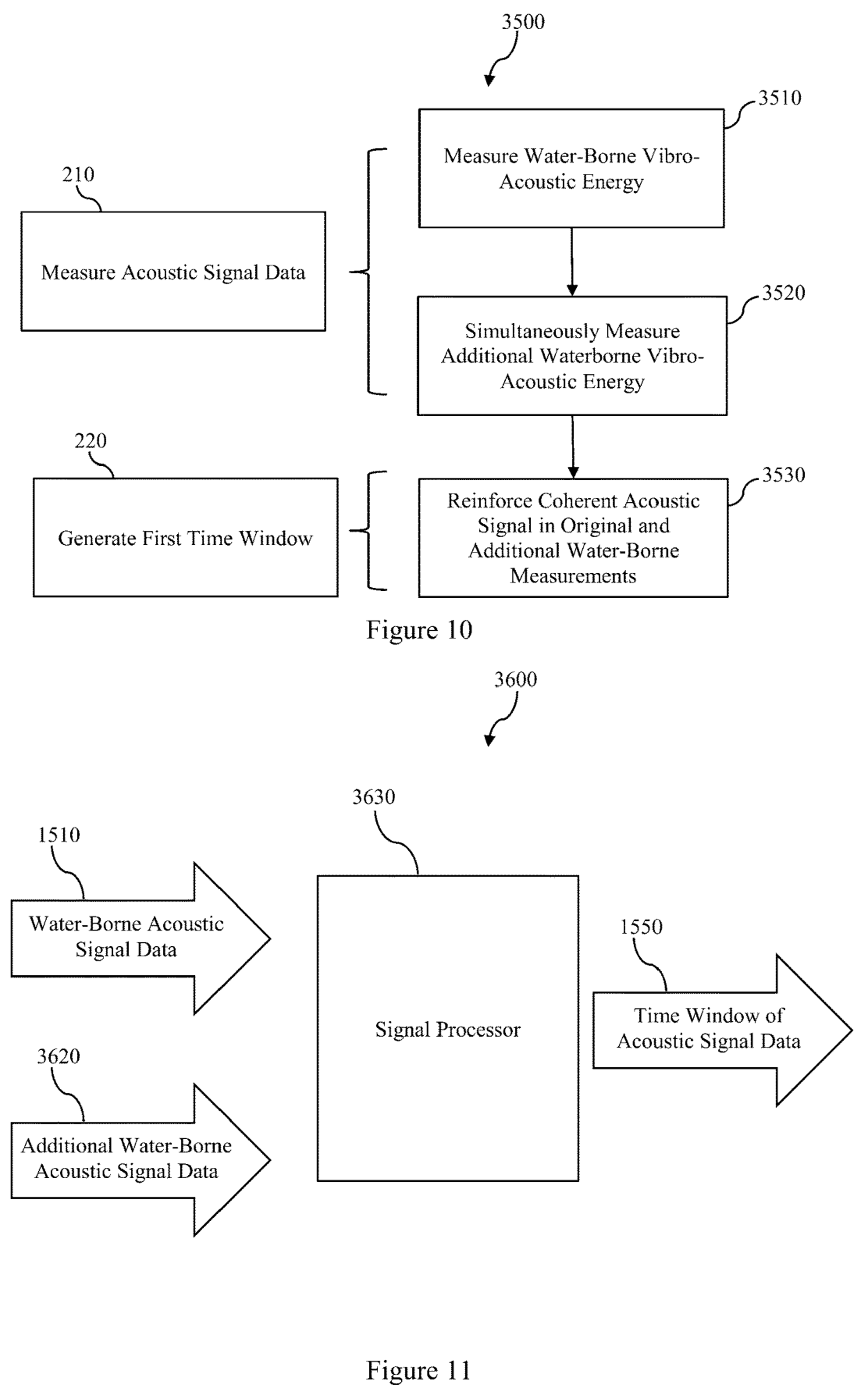

Measure Water-Borne Vibro-Acoustic Energy

210

Measure Acoustic Signal Data

3520

Simultaneously Measure Additional Waterborne Vibro-Acoustic Energy

220

Generate First Time Window

3530

Reinforce Coherent Acoustic Signal in Original and Additional Water-Borne Measurements

Water-Borne Acoustic Signal Data

Signal Processor

1550

Time Window of Acoustic Signal Data

3620

Additional Water-Borne Acoustic Signal Data

METHOD AND SYSTEM FOR DETECTING A STRUCTURAL ANOMALY IN A PIPELINE NETWORK

PRIORITY DOCUMENTS

The present application is a national stage application under 35 U.S.C. 371 and claims the benefit of PCT Application No. PCT/AU2020/000036 having an international filing date of 24 Apr. 2020, which designed the United States, which PCT application claimed the benefit of Australian Provisional Patent Application No. 2019901401 filed 24 Apr. 2019, Australian Provisional Patent Application No. 2019901400 filed on 24 Apr. 2019, the contents of each of which are incorporated herein in by reference in their entireties.

TECHNICAL FIELD

The present disclosure relates to detection of a structural anomaly event in an operational pipeline network. In a particular form, the present disclosure relates to processing acoustic information to determine the presence and characterise the structural anomaly.

BACKGROUND

Water main breaks cause significant problems across the globe. They can lead to traffic interruptions, property damage by direct exposure to high pressure water with associated significant and rapid dangerous flooding, and result in negative publicity for water utilities. In the central business district areas of cities, damage to third party buried telecommunication and power infrastructure caused by uncontrolled main breaks is a significant additional problem as well as the potential damage to infrastructure located in the basements of buildings.

Currently, the management of water main breaks is largely reactive. Uncontrolled main breaks are fixed after visual detection and the emergency deployment of reactive operational repair crews. Due to the urgency created by water unavailability to customers, commercial premises, hospitals and industry and resulting traffic chaos, repairs are often rushed and can fail repeatedly. In some cases, a section of water main may be replaced after several uncontrolled breaks have been experienced. Should current reactive practices continue, the number of uncontrolled water main breaks will likely increase as water pipeline infrastructure ages.

Water utilities worldwide are looking for solutions to reduce uncontrolled water main break rates and improve their service to the public. In recent years, continuous pressure monitoring systems (for transient and/or steady-state pressure management) involving a sensor network have been used and corresponding analysis techniques have been developed to detect and locate pipe main breaks after their occurrences. However, such continuous transient monitoring for main break detection is still a reactive practice and most main breaks are first brought to the attention of the water utility via public reporting rather than through the sensor network.

It would be desirable to provide a more proactive approach which prevents, or at least reduces, the occurrence of uncontrolled pipe main breaks by detecting and fixing the developing pipe cracks before uncontrolled failures.

SUMMARY

In a first aspect, the present disclosure provides a method for detecting a structural anomaly in a pipeline supply network, the pipeline supply network configured to supply fluid to multiple receiving locations, comprising:

receiving acoustic signal data from a selected location in the pipeline supply network;

generating a first time window of acoustic signal data based on the acoustic signal data;

benchmarking the first time window of acoustic signal data with respect to historical background acoustic signal data characterising the pipeline supply network to generate a corresponding background benchmarked first time window of acoustic signal data; and determining an anomaly measure for the background benchmarked first time window of acoustic signal data, wherein the anomaly measure indicates a presence of the structural anomaly.

In another form, benchmarking the first time window of acoustic signal data with respect to historical background acoustic signal data characterising the pipeline supply network includes:

determining an estimated spectral content difference between the first time window of acoustic signal data and the historical background acoustic signal data; and removing the spectral content difference from the first time window of acoustic signal data to generate the corresponding background benchmarked first time window of acoustic signal data.

In another form, determining an estimated spectral content difference between the first time window and the background acoustic signal data includes:

determining the spectral content of the historical background acoustic signal data;

determining the spectral content of the first time window of acoustic signal data; and determining in frequency space the difference between the spectral content of the background acoustic signal data and the spectral content of the first time window of acoustic signal data.

In another form, removing the spectral content difference from the first time window of acoustic signal data includes:

applying in frequency space the spectral content difference to the spectral content of the first time window of acoustic signal data to generate a spectrally modified first time window; and transforming the spectrally modified first time window to the time domain to generate the corresponding background benchmarked first time window of acoustic signal data.

In another form, the method further comprises on determining the presence of the structural anomaly in the background benchmarked first time window of acoustic signal data then:

generating a subsequent second time window of acoustic signal data;

benchmarking the subsequent second time window of acoustic signal data with respect to the first time window of acoustic signal data to generate a corresponding comparison benchmarked second time window of acoustic signal data;

determining the anomaly measure for the comparison benchmarked second time window of acoustic signal data; and characterising the structural anomaly by comparing the anomaly measure determined for the background benchmarked first time window of acoustic signal data with the anomaly measure determined for the comparison benchmarked second time window of acoustic signal data.

In another form, characterising the structural anomaly includes determining whether the structural anomaly is increasing, reducing or remains unchanged for a time period between the first and second time windows.

In another form, benchmarking the subsequent second time window of acoustic signal data with respect to the first time window of acoustic signal data includes:

determining the spectral content difference between the second time window of acoustic signal data and the first time window of acoustic signal data; and removing the spectral content difference from the second time window of acoustic signal data to generate the corresponding comparison benchmarked second time window of acoustic signal data.

In another form, determining the spectral content difference between the second time window and the first time window includes:

determining the spectral content of the first time window of acoustic signal data;

determining the spectral content of the second time window of acoustic signal data; and determining in frequency space the difference between the spectral content of the first time window of acoustic signal data and the spectral content of the second time window of acoustic signal data.

In another form, removing the spectral content difference from the second time window of acoustic signal data includes:

applying in frequency space the spectral content difference to the spectral content of the second time window of acoustic signal data to generate a spectrally modified first time window; and transforming the spectrally modified second time window to the time domain to generate the corresponding background benchmarked second time window of acoustic signal data.

In another form, the method comprises:

benchmarking the second time window of acoustic signal data with respect to background acoustic signal data characterising the pipeline supply network to generate a corresponding background benchmarked second time window of acoustic signal data; and determining the anomaly measure for the background benchmarked second time window of acoustic signal data.

In another form, the method further comprises on determining that the background benchmarked first time window of acoustic signal data does not indicate the presence of the structural anomaly then supplementing the background acoustic signal data with the first time window of acoustic signal data to further characterise the pipeline supply network.

In another form, measuring acoustic signal data at the selected location includes measuring at the selected location fluid-borne vibro-acoustic energy transferred by fluid moving through the pipeline supply network to generate fluid-borne acoustic signal data.

In another form, generating the first time window of acoustic signal data includes enhancing the fluid-borne acoustic signal data with other simultaneously measured synchronised acoustic signal data.

In another form, enhancing the fluid-borne acoustic signal data with other simultaneously measured synchronised acoustic signal data includes:

simultaneously measuring environmental vibro-acoustic energy proximal to the selected location to generate synchronised environmental acoustic signal data; and processing the fluid-borne acoustic signal data to remove from the fluid-borne acoustic signal data, a coherent acoustic signal present in both the fluid-borne and the synchronised environmental acoustic signal data for the time window.

In another form, processing the fluid-borne acoustic signal to remove the coherent acoustic signal includes adaptively filtering the fluid-borne acoustic signal data with respect to the synchronised environmental acoustic signal data by a LMS filter that seeks to minimise an error between an output signal and a desired signal comprising the fluid-borne acoustic signal data.

In another form, processing the fluid-borne acoustic signal to remove the coherent acoustic signal includes determining a non-coherent output power of the fluid-borne acoustic signal data with respect to synchronised environmental acoustic signal data.

In another form, simultaneously measuring environmental vibro-acoustic energy proximal to the selected location includes simultaneously measuring air-borne vibro-acoustic energy in the space proximal to the selected location to generate synchronised environmental acoustic signal data comprising air-borne acoustic signal data.

In another form, simultaneously measuring environmental vibro-acoustic energy proximal to the selected location includes simultaneously measuring ground-borne vibro-acoustic energy in the ground proximal to the selected location to generate synchronised environmental acoustic signal data comprising ground-borne acoustic signal data.

In another form, enhancing the fluid-borne acoustic signal data with other simultaneously measured acoustic signal data includes:

simultaneously measuring fluid-borne vibro-acoustic energy at a different location to the selected location to generate synchronised additional fluid-borne acoustic signal data; and processing the fluid-borne acoustic signal to reinforce in the fluid-borne acoustic signal data, a coherent acoustic signal present in both the fluid-borne and synchronised additional fluid-borne acoustic signal data for the time window.

In another form, processing the fluid-borne acoustic signal to reinforce a coherent acoustic signal present in both the fluid-borne and synchronised additional fluid-borne acoustic signal data includes adaptively filtering the fluid-borne acoustic signal data with respect to the synchronised additional fluid-borne acoustic signal data by a LMS filter that seeks to minimise an error between an output signal and a desired signal comprising the fluid-borne acoustic signal data.

In another form, processing the fluid-borne acoustic signal to reinforce the coherent acoustic signal includes determining a coherent output power of the fluid-borne acoustic signal data with respect to synchronised additional fluid-borne acoustic signal data.

In another form, the first and second time windows of acoustic data are selected from a time when the corresponding background acoustic noise of the pipeline supply network is below a minimum threshold.

In another form, the first and second time windows of acoustic data are selected from acoustic signal data measured at the same time of day.

In another form, the structural anomaly comprises a leak in the pipeline supply network.

In another form, the pipeline supply network comprises a cast iron pipe, and wherein the structural anomaly includes a circumferential or longitudinal crack in the cast iron pipe.

In another form, the method further comprises measuring the acoustic signal data at the selected location.

In a second aspect, the present disclosure provides a detection system for detecting a structural anomaly in a pipeline supply network, the pipeline supply network configured to supply fluid to multiple receiving locations, comprising:

a sensor network including a plurality of measurement stations for measuring acoustic signal data at a plurality of locations in the pipeline supply network;

one or more data processors operatively connected to the sensor network and configured to carry out the method in accordance with the first aspect of the disclosure.

In a third aspect, the present disclosure provides a measurement station for measuring vibro-acoustic energy in a pipeline supply network, comprising:

a fluid-borne vibro-acoustic sensing arrangement for measuring fluid-borne acoustic energy transferred by fluid moving through the pipeline supply network at a selected location to generate fluid-borne acoustic signal data; and an environmental acoustic sensing arrangement for simultaneously measuring environmental vibro-acoustic energy proximal to the selected location to generate synchronised environmental acoustic signal data.

In another form, the fluid-borne vibro-acoustic sensing arrangement comprises one or more of:

an internal fluid acoustic sensor immersed in the fluid to directly measure fluid-borne acoustic energy; or an external fluid acoustic sensor coupled to the pipeline supply network to indirectly measure fluid-borne acoustic energy.

In another form, the environmental acoustic sensing arrangement comprises one or more of:

a ground acoustic sensor for measuring ground-borne vibro-acoustic energy transferred through the ground proximal to the selected location; or an air acoustic sensor for measuring air-borne vibro-acoustic energy in the space proximal to the selected location.

In a fourth aspect, the present disclosure provides a method for generating acoustic signal data from a pipeline supply network, the pipeline supply network configured to supply fluid to multiple receiving locations, comprising:

receiving fluid-borne acoustic signal data from a fluid-borne vibro-acoustic sensing arrangement for measuring fluid-borne acoustic energy transferred by fluid moving through the pipeline supply network at a selected location;

receiving synchronised environmental acoustic signal data from an environmental acoustic sensing arrangement for simultaneously measuring environmental vibro-acoustic energy proximal to the selected location; and enhancing the fluid-borne acoustic signal data with the synchronised environmental acoustic signal data.

In another form, enhancing the fluid-borne acoustic signal data with the synchronised environmental acoustic signal data includes processing the fluid-borne acoustic signal data to remove from the fluid-borne acoustic signal data a coherent acoustic signal present in both the fluid-borne and the synchronised environmental acoustic signal data.

In a fifth aspect, the present disclosure provides a method for generating acoustic signal data from a pipeline supply network, the pipeline supply network configured to supply fluid to multiple receiving locations, comprising:

receiving fluid-borne acoustic signal data from a first fluid-borne vibro-acoustic sensor for measuring fluid-borne acoustic energy transferred by fluid moving through the pipeline supply network at a selected location;

receiving synchronised additional fluid-borne acoustic signal data from a second fluid-borne vibro-acoustic sensor for measuring fluid-borne acoustic energy transferred by fluid moving through the pipeline supply network proximal to the selected location; and enhancing the fluid-borne acoustic signal data with the synchronised additional vibro-acoustic signal data.

In another form, enhancing the fluid-borne acoustic signal data with the synchronised additional vibro-acoustic signal data includes processing the fluid-borne acoustic signal to reinforce in the fluid-borne acoustic signal data, a coherent acoustic signal present in both the fluid-borne and synchronised additional fluid-borne acoustic signal data.

BRIEF DESCRIPTION OF DRAWINGS

Embodiments of the present disclosure will be discussed with reference to the accompanying drawings wherein:

FIG. 5 is a flowchart of a method for measuring acoustic signal data at a selected location to generate a first time window of acoustic signal data in accordance with an illustrative embodiment;

FIG. 6 is a system overview diagram of a coherent signal removal system in accordance with an illustrative embodiment;

FIG. 10 is a flowchart of a method for measuring acoustic signal data at a selected location to generate a first time window of acoustic signal data in accordance with an illustrative embodiment;

FIG. 11 is a system overview diagram of a coherent signal enhancement system in accordance with an illustrative embodiment;

In the following description, like reference characters designate like or corresponding parts throughout the figures.

DESCRIPTION OF EMBODIMENTS

Figure 1:
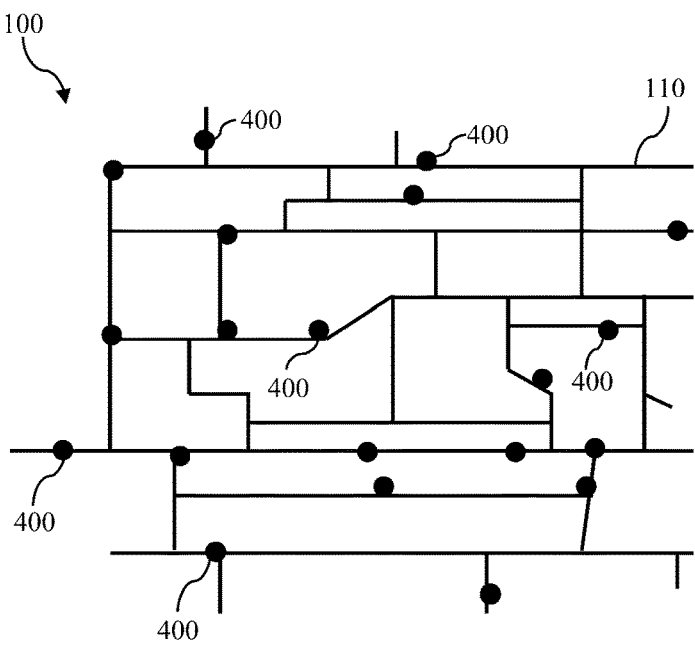
FIG. 1 is a figurative view of a pipeline supply network 100 in accordance with an illustrative embodiment.

Referring now to FIG. 1, there is shown a figurative view of a pipeline supply network 100 configured to supply fluid to multiple receiving locations according to an illustrative embodiment. In this example pipeline supply network system 100 consists of a network of pipes 110 designed to deliver water to receiving locations such as buildings and homes and the like and where the pipes 110 are located below ground and generally align with the road and street system for traffic. In accordance with the present disclosure, the pipeline supply network system 100 is instrumented to include one or more measurement stations 400 located at selected locations in the pipeline supply network 100 where the measurement stations 400 each measure acoustic signal data at the respective location.

As would be appreciated, while the present disclosure is described in the context of a utility scale pipeline network for the supply of water, the methods and systems disclosed may also be applied to any pipeline supply network which is designed to supply fluid to multiple receiving locations. Examples include, but are not limited to, petroleum refinery, storage and supply, processing factories, wine making and storage, minerals processing, gas supply networks, hot water heating supply networks, or airport fuel systems.

Figure 2:
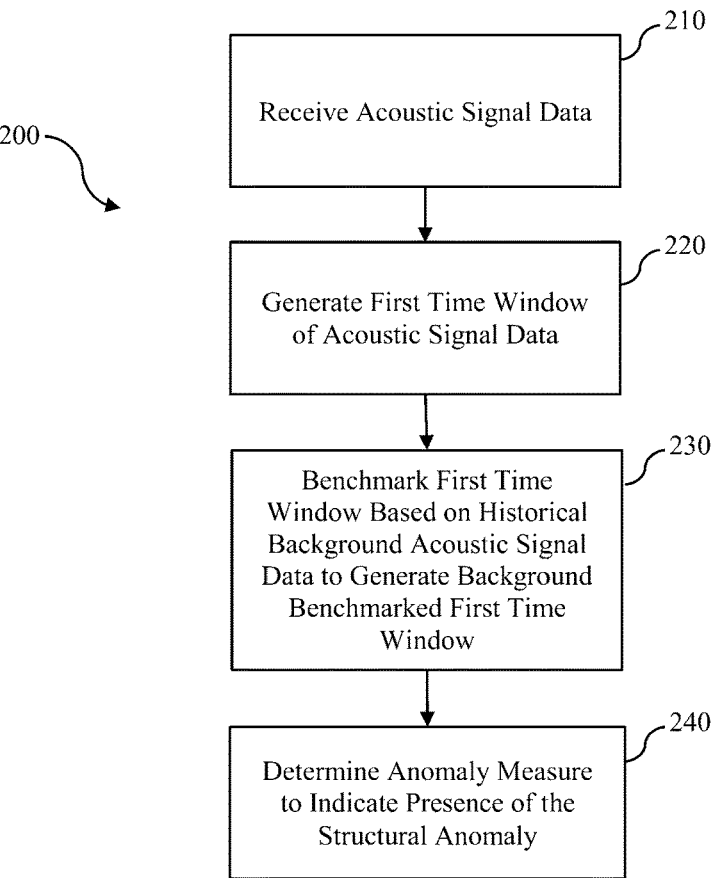
FIG. 2 is a flowchart of a method for detecting a structural anomaly in a pipeline supply network in accordance with an illustrative embodiment.

Referring now to FIG. 2, there is shown a flowchart of a method 200 for detecting a structural anomaly in a pipeline supply network according to an illustrative embodiment. In this example method 200 may be applied to a pipeline supply network 100 such as illustrated in FIG. 1.

By way of overview, method 200 comprises at step 210 receiving acoustic signal data at a selected location in the pipeline supply network 100 and then at step 220 generating a first time window of acoustic signal data. This window of acoustic signal data at step 230 is benchmarked with respect to historical background acoustic signal data that characterises the operation of the pipeline supply network 100 to generate a corresponding background benchmarked first time window of acoustic signal data. As will be seen below, the background acoustic noise signal may be based on previous measurements at the selected location, or at a related location or a composite measure characterising the background behaviour of the pipeline supply network 110. At step 240, an anomaly measure is determined based on this background benchmarked acoustic signal data where the anomaly measure is selected to indicate the presence of a structural anomaly in the pipeline supply network 100.

Figure 3:
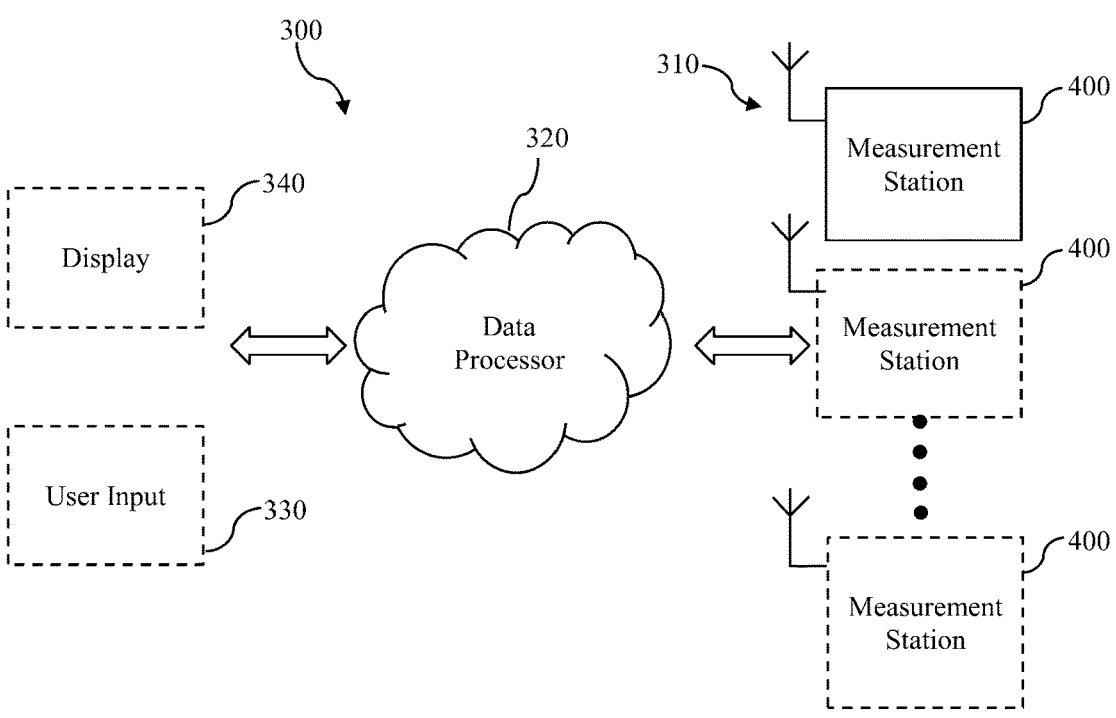
FIG. 3 is a system overview diagram of a detection system for detecting a structural anomaly in a pipeline network in accordance with an illustrative embodiment.

Referring now to FIG. 3, there is shown a system view of a detection system 300 operable in one example to implement detection method 100. Again by way of overview, detection system 300 includes one or more measurement stations 400 deployed throughout the pipeline network 100 and configured to measure acoustic signal data at respective locations in the pipeline network 100. This information is then transferred to a data processor 320 and processed in accordance with method 100 and results may be deployed on optional display 340 and input may be provided by optional user input 330 as required. In one example embodiment, one or more of the measurements stations 400 may be time synchronised to one or more of the other measurement stations 400.

Figure 4:
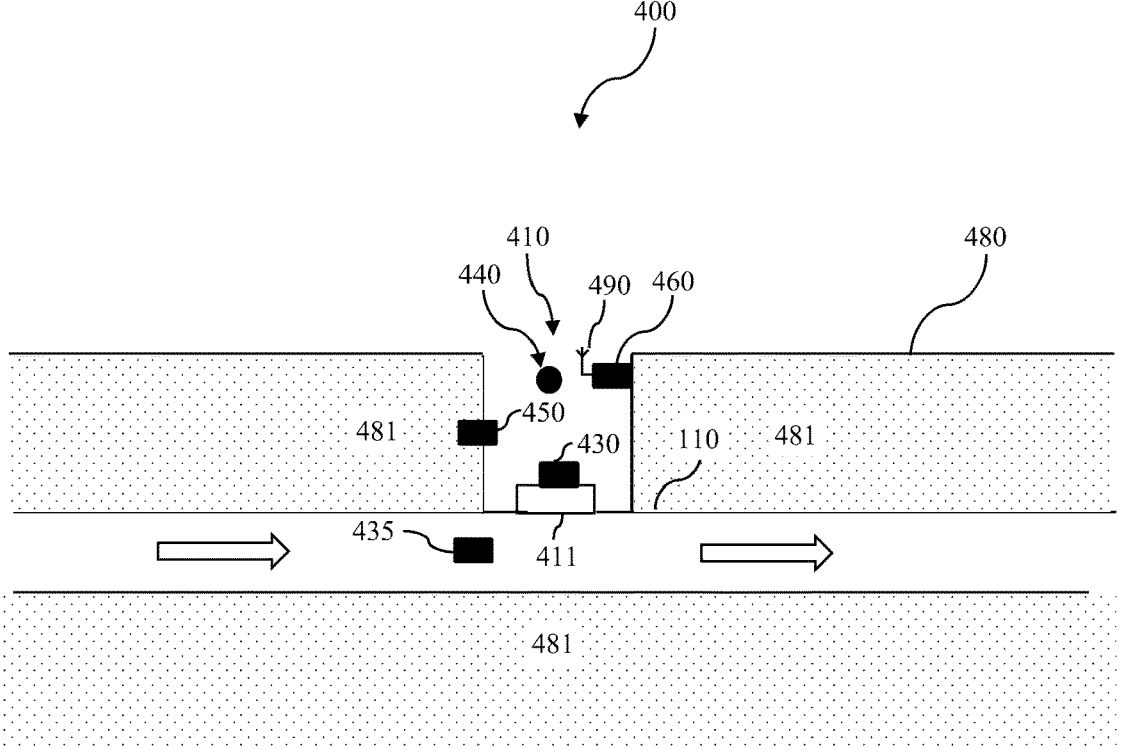
FIG. 4 is a figurative view of a measurement station in accordance with an illustrative embodiment.

Referring back to FIG. 2, at step 210, acoustic signal data is measured at or received from a selected location in the pipeline network 100. In one example, the acoustic signal data is measured by a measurement station 400 as depicted in FIG. 3. Referring now to FIG. 4, there is shown a figurative view of a measurement station 400 according to an illustrative embodiment. In this example, measurement station 400 is located at an underground access valve chamber 410 which could be for, as an example, a fire hydrant valve, an air valve or a control valve which is located below the surface 480 (eg, a road, path or the like) providing access to valve 411 of the pipe or pipe component 110 of the pipeline network 100.

As would be appreciated, valves are generally an important component of a pipeline network 100 as they provide an isolation capability to limit water to flow in certain zones, sometimes referred to as pressure zones or demand management zones, and may be employed when there is a burst or leak or when maintenance is required. As such, valves are generally regularly distributed throughout a pipeline network and provide a convenient access point especially where all or part of the pipeline network is below ground. It would be understood, however, that measurement station 400 may be deployed at any suitable location providing access to a pipe 110 of the pipeline network including, but not limited to, pipeline components such as a fire hydrant, fire plug, valve chamber, air valve, inspection point or flow meter, fire service connection or water supply connection. In other examples, a customised access point may be constructed in order to provide access to the pipe 110 at a desired location.

Measurement station 400 comprises a number of sensors including, but not limited to, a fluid acoustic sensor configured to measure at the selected location fluid-borne vibro-acoustic energy transferred by fluid moving through the pipeline network 100 at the selected location at pipe 110 to generate fluid-borne acoustic signal data.

This fluid-borne vibro-acoustic energy may arise from a number of sources including, but not limited to:

the flow of the fluid through the pipeline network including the interaction of the liquid with various components of the pipeline, eg pipe wall, valves, distribution points, water meters etc;

the interaction of fluid flowing through the pipeline network with any structural anomaly such as a leak resulting in additional flows of fluid departing the network; or any source of acoustic energy that is operably connected to the pipeline network and transferrable by the fluid moving through the pipeline network, eg, general environmental noise such as traffic, plant equipment, night clubs, tram operation, bus operation, train operation, functions, excavation work, construction site activities, concerts, car races and industrial water use.

In one example, a fluid acoustic sensor is configured as an internal fluid acoustic sensor 435 in the form of a hydrophone that may be situated in the fluid that is flowing through pipe 110 to directly measure the fluid-borne vibro-acoustic energy transferred by fluid moving through the pipeline supply network 100. In this example, the hydrophone type sensor is mounted on a flexible or rigid insertion tube that is inserted into the pipe or pipe connection through a specifically manufactured plate or cap on an air valve or fire hydrant or fire plug. In one non-limiting example, a suitable hydrophone type sensor could be a Teledyne Reson hydrophone TC4037 spherical reference hydrophone with a useable frequency range from 1 Hz to 100 kHz and a receiving sensitivity −193 dB re 1V/u at 250 Hz.

An internal fluid acoustic sensor 435 of this type is responsive to the acoustic pressure or the pressure gradient or the acoustic particle velocity and as a result to the vibro-acoustic energy of water or fluid moving in pipe 110. In another example, the internal fluid acoustic sensor 435 may comprise an optical fibre based hydrophone array that is configured to be responsive to the acoustic pressure or the pressure gradient or the acoustic particle velocity and as a result to the vibro-acoustic energy of water or fluid moving in pipe 110.

In another example, a fluid acoustic sensor is configured as an external fluid acoustic sensor 430 attached to the exterior of pipe 110 at valve 411 and configured to measure indirectly the fluid-borne acoustic energy transferred by fluid moving through the pipeline supply network 100 as further propagated through and/or along the wall of pipe 110. In one embodiment, external fluid acoustic sensor 430 is an accelerometer. A non-limiting example of this type of external fluid acoustic sensor includes the use of an ultralow frequency seismic accelerometer from Wilcoxon Sensing Technologies with a sensitivity of 10 V/g and an acceleration range of 0.5 g peak and a frequency response from 0.2-1300 Hz. In one example, a specifically constructed plate or cap is employed and fitted to the valve 411 or in other examples to a fire hydrant or fire plug. In another example, the external fluid acoustic sensor may be fitted with a magnetic mounting arrangement for attachment.

External and internal fluid acoustic sensors 430, 435 may be deployed optionally or supplementing each other depending on requirements. As an example, significant local noise generation may impede hydrophone operation.

An example may include the deployment near a water meter or a pump that generates such significant acoustic noise that a hydrophone type internal sensor will be overwhelmed and clip the hydrophone measured signal. As another example, the measurement may commonly occur in a branch off the main pipe. Such branches can act as filters or resonators which may modify the actual signal being observed in the pipe and measurement in the main pipe will need to be undertaken to determine the extent of the modification of the fluid-borne acoustic signal. In another example, a heavily trafficked bus or truck route may produce too much ground induced fluid vibration that a hydrophone type internal fluid acoustic sensor will clip and be unable to effectively measure the acoustic signal.

Where both acoustic sensors 430, 435 are deployed then one of the sensors, say as an example, external fluid acoustic sensor 430 will provide a fluid-borne acoustic signal data at the selected location and internal fluid acoustic sensor 435 will provide additional synchronised fluid-borne acoustic signal data simultaneously measured at a different location. In the example depicted in FIG. 4, both acoustic sensors 430, 435 are located proximal to each other.

Measurement station 400 may also include an environmental acoustic sensor configured to simultaneously measure environmental vibro-acoustic energy proximal to the selected location to generate synchronised environmental acoustic signal data. In one example, environmental acoustic sensor includes an air acoustic sensor 440 configured to simultaneously measure synchronised air-borne vibro-acoustic energy in the space proximal to the selected location such as in valve chamber 410 to generate air-borne acoustic signal data.

While in FIG. 4, air acoustic sensor 440 is shown located in valve chamber 410, in other configurations air acoustic sensor 440 may be located outside of chamber 410. In another example, air acoustic sensor 440 includes baffling or other isolation arrangements to further prevent the sensor from measuring vibrations from the pipe or the ground. In one non-limiting example, a suitable air acoustic sensor includes a GRAS 40PH CCP free-field array microphone with a frequency range of 10 to 20 KHz, a dynamic range of 32 dB(A) to 135 dB and a sensitivity of 50 mV/Pa.

In another non-limiting example, air acoustic sensor 440 may include an accelerometer attached to a plate but isolated from the pipe and the valve chamber. Such an accelerometer may include, but not be limited to, an ultralow frequency seismic accelerometer from Wilcoxon Sensing Technologies with a sensitivity of 10 V/g and an acceleration range of 0.5 g peak and a frequency response from 0.2-1300 Hz.

Air acoustic sensor 440 is configured to measure air-borne environmental acoustic sounds. In the case of a utility scale water supply network, this will include background noise arising from traffic which will vary in intensity and other sounds including, but not limited to: population noise such as people talking, high heeled shoes or pets; functions such as wedding or other gatherings; locations such as night clubs or construction sites; audible traffic signalling operations, vehicle noise such as engine noise, trams, tyre road interaction, brake noise; or plant equipment such as air conditioners or generators.

In another example, environmental acoustic sensor includes a ground acoustic sensor 450 which is configured to measure simultaneously ground-borne vibro-acoustic energy transferred through the ground 481 proximal to the selected location to generate synchronised ground-borne acoustic signal data. Suitable examples of a ground acoustic sensor 450 include, but are not limited to vibration sensors such as accelerometers or seismic sensors (eg geophone), strain gauges or optical fibres that are configured to measure ground-borne noise. In various examples, ground acoustic sensor 450 may be magnetically attached to the valve chamber wall, glued there, or fastened with a bolt. In other embodiments, ground acoustic sensor 450 may be located in the ground outside the chamber, accessed through a hole in the chamber wall, or placed there when the chamber is constructed.

Measurement station 400 in this example further includes a data processor in the form of a data acquisition (DAQ) module 460 for receiving and processing the measured acoustic signal data. In one example, the DAQ simultaneously receives and applies appropriate time stamps to synchronise the acoustic signal data from each of the sensors for later processing based on their synchronised measurement. In another example, the sensors may incorporate an appropriate timer synchronised to the other sensors and the locally synchronised data may be transferred without requiring further time-stamping. In one example, one or more of the sensors include a GPS module capable of providing this time synchronisation capability. An example GPS module that may be employed includes, but is not limited to, a National Instruments™ NI-9467 C Series Synchronization Module which is able to provide accurate time synchronisation and data time stamping.

As would be appreciated, the various sensors or DAQ module 460 may be configured to measure or store acoustic signal data commencing at a predetermined time for a predetermined time period and either store the data locally at the respective sensor or DAQ module 460 and/or transfer this data to a central location by wireless or other means as will be discussed below. In another example, one or more of the sensors are configured to buffer and wirelessly send data for further storage and processing.

In one example, generating the first time window of acoustic signal data includes enhancing the fluid-borne acoustic signal data with other simultaneously measured acoustic signal data based on environmental or additional fluid-borne acoustic signal data that has been simultaneously measured and synchronised with the fluid-borne acoustic signal data.

Referring now to FIG. 5, there is shown a flowchart of a method 500 for measuring acoustic signal data and then generating a first time window of acoustic signal data according to an illustrative embodiment corresponding to steps 210 and 220 of FIG. 2. At step 510, the fluid-borne vibro-acoustic energy is measured by a fluid acoustic sensor 430, 435 such as described previously to generate fluid-borne acoustic signal data. As referred to previously, the fluid-borne vibro-acoustic energy may arise from a number of potential sources and not only result from the flow of fluid in the immediate vicinity of the location of the acoustic sensor.

At step 520, the environmental vibro-acoustic energy is simultaneously measured by a sensor such as air acoustic sensor 440 and/or ground acoustic sensor 450 to generate synchronised environmental acoustic signal data.

At step 530, the fluid-borne acoustic signal is processed to remove a coherent acoustic signal present in both the fluid-borne and the synchronised environmental acoustic signal data from the fluid-borne acoustic signal data for the relevant time window.

Referring now to FIG. 6, there is shown a system overview diagram of a coherent signal removal system 1500 for removing the coherent acoustic signal that is present in both the fluid-borne and synchronised environmental vibro-acoustic energy measurements according to an illustrative embodiment. Coherent signal removal processing system 1500 includes a signal processing module 1530 receiving as inputs the fluid-borne acoustic signal data 1510 and the synchronised environmental acoustic signal data 1520 and which functions to output a time window of acoustic signal data 1540 where the coherent acoustic signal has been removed from the fluid-borne acoustic signal data.

In one example, the acoustic signal data 1510, 1520, 1550 may be configured in a "WAV" file format. As would be appreciated, the WAV file format is a lossless raw audio format (typically uncompressed) configured to store acoustic or audio data and includes fields specifying the sample rate and bit rate. As such, a WAV file is a convenient representation of a time window of acoustic signal data. As would be appreciated, other lossless audio format may be adopted depending on requirements including, but not limited to, Windows Media Audio (WMA), Apple Lossless Audio Codec (ALAC) or Free Lossless Audio Codec (FLAC).

In one embodiment, signal processing module 1530 is based on adaptive noise suppression where a filter is dynamically configured to filter or remove the coherent acoustic signal from the fluid-borne acoustic signal data 1510. In one example, a least means square (LMS) filter is employed where the environmental acoustic signal data 1520 comprises the input which may be represented as a vector of values u(n) where n is the current time index with n ranging from 1, . . . , N defining a time window. In this example, fluid-borne acoustic signal data 1510 may similarly be represented as a vector of values d(n) comprising the desired response at given time step n.

In this embodiment, the LMS filter implements a finite impulse response (FIR) filter that seeks to minimise an error e(n) between the output signal y(n) and the desired signal, d(n), ie e(n)=d(n)−y(n). In this configuration, the vector of values e(n) will correspond to a time window of acoustic signal data 1550 where the coherent acoustic signal present in both inputs 1510, 1520 has been removed. In another embodiment, the LMS filter may comprise a normalised LMS filter. In another example, the LMS filter may implement an infinite impulse response (IIR) filter.

As would be appreciated, the removal may be implemented "online" and in real time to process the fluid-borne acoustic signal data locally at a given measurement station 400, say by DAQ module 460, to remove the coherent acoustic signal present in both the fluid-borne and the synchronised environmental acoustic signal data. In other embodiments, the relevant synchronised acoustic signal data streams may be transferred by wireless or wired network arrangement to a central data store for subsequent processing offline.

Figure 7:
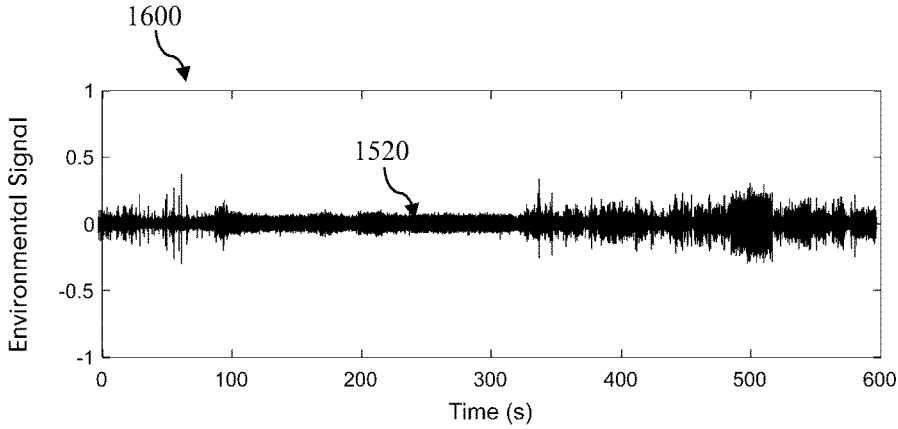
FIG. 7 is a plot of environmental acoustic signal data in accordance with an illustrative embodiment.
Figure 8:
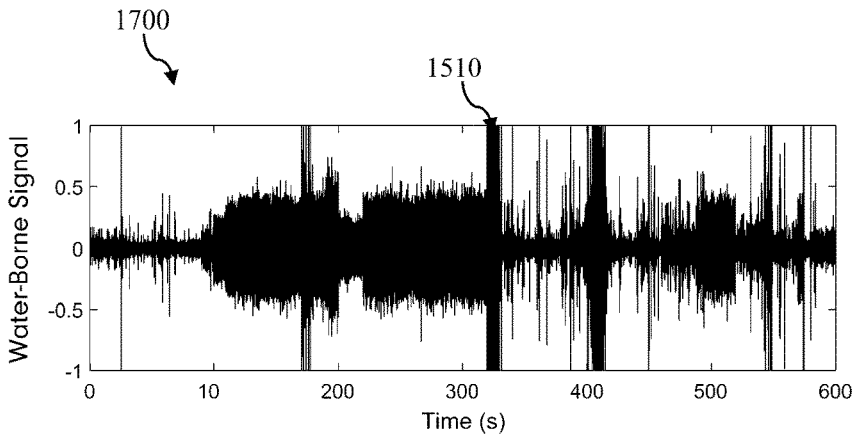
FIG. 8 is a plot of fluid-borne acoustic signal data in accordance with an illustrative embodiment.

Referring now to FIG. 7, there is shown a plot 1600 of environmental acoustic signal data 1520 according to an illustrative example. In this example, environmental acoustic signal data 1520 is measured by a ground acoustic sensor and plot 1600 depicts a time window having a duration of 600 seconds. Similarly, referring now to FIG. 8, there is shown a plot 1700 of fluid-borne acoustic signal data 1510 as measured by a fluid acoustic sensor again having a duration of 600 seconds. In one example, the environmental acoustic signal data is measured at the barrel of a fire hydrant.

Figure 9:
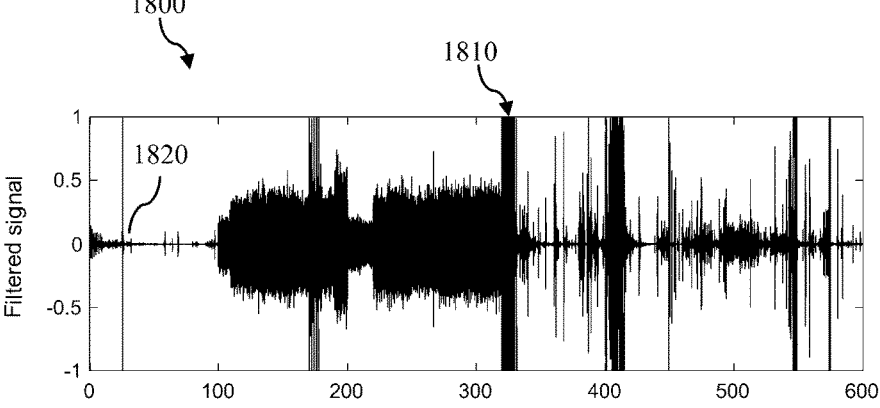
FIG. 9 is a plot of the generated time window of filtered acoustic signal data showing the removal of the coherent acoustic signal in accordance with an illustrative embodiment.

Referring now to FIG. 9, there is shown a plot 1800 of the generated time window of filtered acoustic signal data 1810 depicting the removal of the coherent acoustic signal from the fluid-borne acoustic signal data according to an illustrative embodiment. In this example implementation, signal processing module 1530 reads the WAV files corresponding to the fluid-borne acoustic signal data 1510 and environmental acoustic signal data 1520 having a sampling rate of 4681 Hz and comprising 16 bit values and buffers this data into 32 element blocks which are then processed by the adaptive filter to generate continuously the filtered acoustic signal data 1550 which once the input acoustic signal data 1510, 1520 has been processed will correspond to the time window of acoustic signal data. As can be seen in FIG. 9, there is an initial period 1820 in the filtered acoustic signal data 1810 corresponding to the time it takes for the weighting coefficients of the adaptive filter to "adapt".

While the above approach is applicable in the time domain, in another embodiment an approach based on coherence in frequency space may be adopted.

The coherence between two signals x(t) and y(t) may be defined as:

$$C_{xy}(f) = \frac{|G_{xy}(f)|^2}{G_{xx}(f)G_{yy}(f)} \qquad \text{Equation 1}$$

where $G_{xy}(f)$ is the cross-spectral density between x and y, and $G_{xx}(f)$ and $G_{yy}(f)$ are the autospectral densities of x and y respectively and magnitude of the spectral density is denoted as $|G|$. The coherence function then estimates the extent to which y(t) may be predicted from x(t) by an optimum linear least squares function.

If $C_{xy}(f)$ is less than one, but greater than zero, then this may indicate either that noise is entering the measurements, that the assumed function relating x(t) and y(t) is not linear, or that y(t) is producing output due to input x(t) as well as other inputs. If the coherence is equal to zero, it is an indication that x(t) and y(t) are completely unrelated. In the case of acoustic waves or energy travelling in a pipeline supply network of the type, as contemplated by the present disclosure, these systems may be treated as being linear to a good approximation provided oscillations are small enough not to evoke substantial non-linear friction terms or non-linear transfer functions which is the case here. In any event, the process described above may be extended to higher order spectral terms. In one example, partial coherences for higher order terms may be generated.

As such, the coherence of a linear system represents the fractional part of the output signal power that is produced by the input at that frequency. The quantity $1-C_{xy}$ may then be viewed as an estimate of the fractional power of the output that is not contributed by the input at a particular frequency. This leads to the definition of the coherent output spectrum:

$$G_{vv} = C_{xy}G_{yy} \qquad \text{Equation 2}$$

where $G_{vv}$ provides a spectral quantification of the output power that is correlated with the input but uncorrelated with noise or other inputs.

It follows that if two signals are partially correlated with one another, the energy in each signal which is correlated may be estimated. As an example, the coherent energy in the autospectral density in signal x is given by $COP_{xx}=G_{xx}C_{xy}$ and the coherent energy in the autospectral density in signal y is given by $COP_{yy}=G_{yy}C_{xy}$.

The complement to this, is that energy arising from noise and other sources is given by the non-coherent output power; for the x signal this is defined as $NCOP_{xx}=G_{xx}(1-C_{xy})$ and for signal y it is defined by $NCOP_{yy}=G_{yy}(1-C_{xy})$.

The corollary of the previous example is the removal of noise from undesirable sources. For example, consider two signals, the first signal, $x_a$, is from an accelerometer attached to a hydrant (ie, measuring fluid-borne acoustic signal data) and the second signal, $y_m$, is from a microphone near the hydrant (ie, measuring environmental acoustic signal data). As discussed previously, the accelerometer is representative of the acoustic signal travelling in the pipeline which will include an undesirable environmental component contributing to the accelerometer signal which in this example will be measured by the microphone.

It follows from the coherence approach that $NCOP_{x_ax_a}=G_{x_ax_a}(1-C_{x_ay_m})$ will represent the power spectral density of the accelerometer that is uncorrelated with the microphone effectively removed any coherent noise that is common to both. As an example, after the acoustic signal data has been digitally acquired, the time series is divided into sequences of $2^n$ samples and then windowed, for example by employing a Hanning window, and the FFT applied to each sequence. These Fourier transforms are then averaged and then used to obtain the functions referred to above, eg $NCOP_{x_ax_a}$.

This approach may be extended further to where there are two environmental acoustic signals, eg, a ground acoustic sensor (eg, an accelerometer) on the ground measuring ground-borne acoustic signal data $x_a$, and $x_m$ which represents a microphone near the hydrant measuring air-borne acoustic signal data. In this example, the fluid acoustic sensor (eg, hydrophone in the hydrant) measures fluid-borne acoustic signal data $y_h$. Then, if ground-borne acoustic signal data $x_a$, and air-borne acoustic signal data $x_m$ are not correlated with one another, then the component of the signal in the fluid-borne acoustic signal data $y_h$ associated with the environmental noise is given by $COP_{y_hy_h}=G_{y_hy_h}(C_{x_my_h}+C_{x_ay_h})$ and the component in the signal in the fluid-borne acoustic signal data not associated with environmental noise, that is the enhanced signal where the coherent noise has been removed is given by $NCOP_{y_hy_h}=G_{y_hy_h}(1-C_{x_my_h}-C_{x_ay_h})$.

As would be appreciated, removing the coherent noise in fluid-borne vibro-acoustic energy measurements will filter out general environmental noise in the fluid-borne acoustic signal data and as a result increase the sensitivity of this acoustic signal data to detect effects originating from the interaction of the water or fluid flowing through the pipe such as structural anomalies that have occurred or may be occurring in the pipe.

Referring now to FIG. 10, there is shown a flowchart of a method 3500 for measuring acoustic signal data and then generating a first time window of acoustic signal data according to an illustrative embodiment corresponding to steps 210 and 220 of FIG. 2. At step 3510, the fluid-borne vibro-acoustic energy is measured by, in this example, external fluid acoustic sensor 430 to generate fluid-borne acoustic signal data.

At step 3520, the fluid-borne vibro-acoustic energy is simultaneously measured in a different location by internal fluid acoustic sensor 435 to generate synchronised additional fluid-borne acoustic signal data. In this illustrative embodiment, internal fluid acoustic sensor 435 is located proximal to external fluid acoustic sensor 430.

At step 3530, the fluid-borne acoustic signal is processed to reinforce a coherent acoustic signal present in both the fluid-borne and the synchronised additional acoustic signal data in the fluid-borne acoustic signal data for the relevant time window.

Referring now to FIG. 11, there is shown a system overview diagram of a coherent signal enhancing system 3600 for enhancing the coherent acoustic signal that is present in both the original fluid-borne and the additional fluid-borne acoustic energy measurements according to an illustrative embodiment. Coherent signal enhancing system 3600 includes a signal processing module 3630 receiving as inputs the fluid-borne acoustic signal data 1510 and the synchronised additional fluid-borne acoustic signal data 3620 and which functions to output a time window of acoustic signal data 1550 where the coherent acoustic signal present in both sets of fluid-borne acoustic signal data has been enhanced in the fluid-borne acoustic signal data.

As discussed previously, the acoustic signal data 1510, 3620, 1550 may be configured in a "WAV" file format. In one embodiment, signal processing module 3630 is based on adaptive noise suppression where a filter is dynamically configured to enhance the coherent acoustic signal from the fluid-borne acoustic signal data 1510. In one example, a least means square (LMS) filter is employed where the additional fluid-borne acoustic signal data 3620 comprises the input which may be represented as a vector of values u(n) where n is the current time index with n ranging from 1, . . . , N defining a time window. In this example, fluid-borne acoustic signal data 1510 may similarly be represented as a vector of values d(n) comprising the desired response at given time step n.

In this embodiment, the LMS filter implements a finite impulse response (FIR) filter that seeks to minimise an error e(n) between the output signal y(n) and the desired signal, d(n), ie e(n)=d(n)−y(n). In this configuration, the vector of values y(n) will correspond to a time window of acoustic signal data 1550 where the coherent acoustic signal present in both inputs 1510, 3620 has been enhanced. In another embodiment, the LMS filter may comprise a normalised LMS filler. As referred to previously, the LMS filter may implemented as an IIR filter where appropriate.

As would be appreciated, the enhancement of the acoustic signal data may be implemented "online" and in real time to process the fluid-borne acoustic signal data locally at a given measurement station 400 to enhance the coherent acoustic signal present in both the fluid-borne and the synchronised additional fluid-borne acoustic signal data. In other embodiments, the relevant synchronised acoustic data streams may be transferred by wireless or wired network arrangement to a central data store for subsequent processing offline.

In another embodiment, an approach based on coherence in frequency space may be adopted. In one example, where there are two or more measurements of the fluid-borne acoustic signal these may be processed to generate a time window of acoustic signal data where the fluid-borne acoustic signal data is reinforced due to it being strongly correlated.

As an example, consider two signals, $x_a$ which represents an accelerometer on a hydrant configured to measure the fluid-borne acoustic signal data, and $y_h$ which represents a hydrophone located in the hydrant which measures additional fluid-borne acoustic signal data. Then if both signals are representative of the fluid-borne acoustic signal travelling in the pipeline, then $COP_{x_a x_a} = G_{x_a x_a} C_{x_a y_h}$ represents the power spectral density of the accelerometer that is correlated with the hydrophone effectively removing any noise that is not common to both and reinforcing the signal.

As would be appreciated, the above enhancement processes based on simultaneous and synchronised measurement of additional acoustic signal data may be cascaded or run together as appropriate to progressively reinforce the desired fluid-borne acoustic signal or to remove undesired signal components that are commonly measured. It will also be understood that the above techniques may be interchangeably applied in the time domain or frequency domain depending on requirements.

Referring back to FIG. 2, at step 230 the first time window of acoustic signal data is benchmarked with respect to historical background acoustic signal data that characterises the pipeline supply network to in turn generate a corresponding "background benchmarked" first time window of acoustic signal data.

Figure 12:
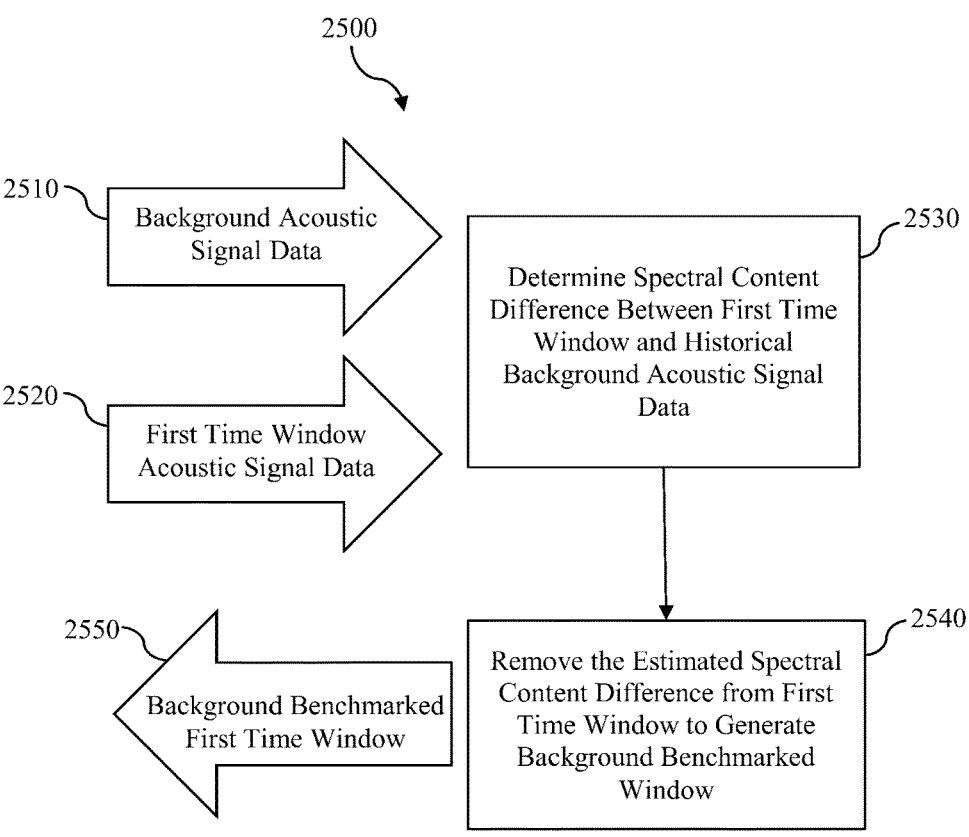
FIG. 12 is a flowchart of a method for benchmarking a time window of acoustic signal data in accordance with an illustrative embodiment.

Referring now to FIG. 12, there is shown a flowchart of a method 2500 for benchmarking a time window of acoustic signal data according to an illustrative embodiment. In this example, a first time window of acoustic signal data 2520 is benchmarked with respect to historical background acoustic signal data 2510. As will be seen in the discussion below, a benchmarking process in accordance with the present disclosure may be applied to any two sets of acoustic signal data. As would be appreciated, in one example the time window of acoustic signal data may have been enhanced or "cleaned" in accordance with the above methods where appropriate additional acoustic signals have been measured by environmental acoustic sensors or further fluid acoustic sensors as the case may be.

In one example, the historical background acoustic signal data is based on acoustic signal data measured at the selected location in the pipeline supply network 100 corresponding to the location of the sensors. In another example, the historical background acoustic noise data may be based on one or more measurements taken from sensors located throughout the pipeline supply network 100. In another example, the historical background acoustic signal data is selected from a predetermined time period relative to the first time window. Examples of this selection of historical background acoustic signal data may include, but not be limited to:

background acoustic signal data chosen from a period 30 days prior to the current time of the first time window as a result taking into account potential monthly variations in the background; or background acoustic signal data chosen from a period 7 days prior to the current time of the first time window as result taking into account potential weekly variations in the background.

In one example, the historical background acoustic signal data is taken from a time period substantially matching the time of day that corresponds to the first time window of acoustic signal data as a result taking into account potential daily variations in the background. In another example, the acoustic signal data is formed from a number of days of historical background acoustic signal data. Examples include, but are not limited to:

background acoustic signal data formed from the first 7 days or otherwise comprising a weekly characterisation of the pipeline supply network; or background acoustic signal data formed over the last 30 days or from the first 15 days of the last 30 days as a result providing a longer term characterisation of the pipeline supply network.

At step 2530, the spectral content difference is determined between the first time window of acoustic signal data 2520 and the historical background acoustic signal data 2510.

Figure 13:
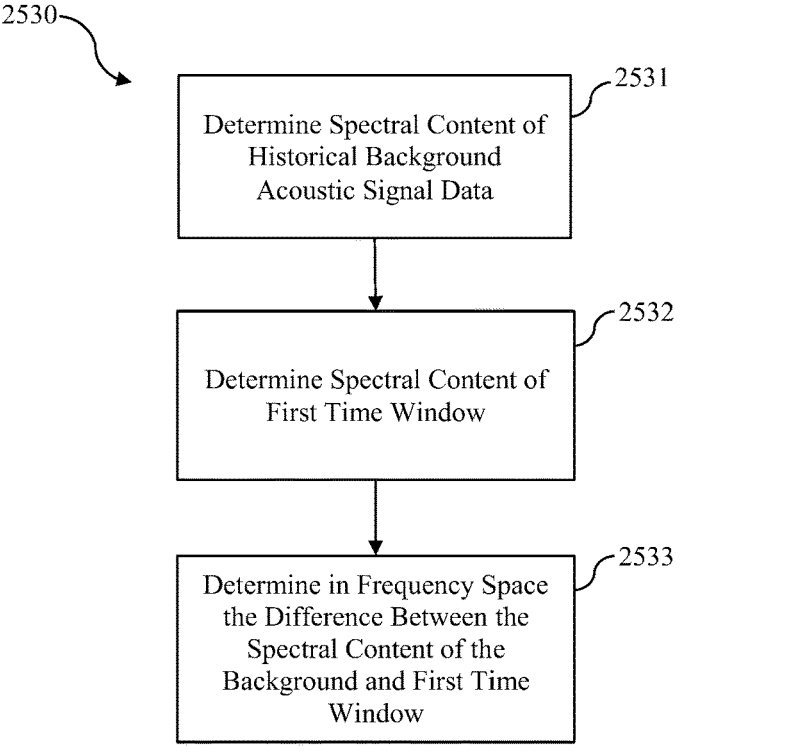
FIG. 13 is a flowchart of a method for determining a spectral content difference in accordance with an illustrative embodiment.

Referring now to FIG. 13, there is shown an example method 2530 for determining the spectral content difference corresponding to step 2530 of FIG. 12 according to an illustrative embodiment.

At step 2531, the spectral content of the historical background acoustic signal data is determined.

In one embodiment, historical background acoustic signal data $x_b(t)$ may comprise a vector $x_b(n)$ having time index n and containing $N_1$ samples as would be acquired by the sensors and associated DAQ system corresponding to a time period $[0, T_1]$ and where the spectral content is determined by forming a spectrogram or spectrum. As such, the relevant sampling frequency $F_s$ is then $N_1/T_1$.

In one example, the vector $x_b(n)$ comprises multiple different segments of historical acoustic signal data that characterise the pipeline supply network as discussed above which are then concatenated together to form an overall vector whose spectral content is to be determined. As an example, $x_b(n)$ may be formed to characterise the pipeline supply network over a particular time of day, a whole day, a week, a month or even a year.

The spectrogram $SX_b$ of $x_b$ is formed by first taking the discrete Fourier Transform $$X_b(k) = \sum_{n=1}^{M-1} x_b(n)e^{-i\frac{2\pi k}{M}n} \text{ where } k = 1, \ldots, M \qquad \text{Equation 3}$$

of the consecutive short windows of the data which might be $[x_b(1), x_b(2), x_b(3), \ldots, x_b(M)]$ and then the window $[x_b(1+\Delta s), x_b(2+\Delta s), x_b(3+\Delta s), \ldots, x_b(M+\Delta s)]$ and so on, with M being the length of the sliding window, and $\Delta s$ being the step between consecutive windows. Then the absolute value of $X_b(k)$ is squared for all the consecutive short windows to yield the spectrogram $SX_b$. Accordingly, the spectrogram $SX_b$ of $x_b$ with window size M is then a matrix whose columns are the DFT of the windows $x_b$ where the rows of $SX_b$ are indexed by frequency and the columns are indexed by time. A window size is determined that allows the spectral content to be characterised in time and depends on the sample frequency. In one non-limiting example, a window size of 1024 may be adopted where a sampling frequency of 4681 Hz has been originally employed. As this process is not a coherent method, long windows are not necessarily required to capture the impulse response function and as such the window size is only required for resolving broad frequency structures in the spectrum.

At step 2532, the spectral content of the first time window of acoustic signal data is determined. By analogy, the first time window of acoustic signal data $x_p(t)$ may comprise a vector $x_p(n)$ having time index n and containing $N_2$ samples as would be acquired by the sensors and associated DAQ system corresponding to a time period $[0, T_2]$ and the spectral content is determined by forming a spectrogram or spectrum. In this case, the relevant sampling frequency $F_s$ is then $N_2/T_2$. As would be appreciated, interpolation techniques may be used to vary the size of vectors and the associated sampling frequencies as required.

The spectrogram $SX_p$ of $x_p$ is then formed by first taking the discrete Fourier Transform $$X_b(k) = \sum_{n=1}^{M-1} x_p(n)e^{-i\frac{2\pi k}{M}n} \text{ where } k = 1, \ldots, M \qquad \text{Equation 4}$$

of the consecutive short windows of the data which might be $[x_p(1), x_p(2), x_p(3), \ldots, x_p(M)]$ and then the window $[x_p(1+\Delta s), x_p(2+\Delta s), x_p(3+\Delta s), \ldots, x_p(M+\Delta s)]$ and so on, with M being the length of the sliding window, and $\Delta s$ being the step between consecutive windows. Then the absolute value of $X_p(k)$ is squared for all the consecutive short windows to yield the spectrogram $SX_p$. Accordingly, the spectrogram $SX_p$ of $x_p$ with window size M is then a matrix whose columns are the DFT of the windows $x_p$ where the rows of $SX_p$ are indexed by frequency and the columns are indexed by time.

At step 2533, the difference between the spectral content of the background acoustic signal data 2510 and the spectral content of the first time window of acoustic signal data 2520 is determined. In one example, the expected background spectrum $\mu X_b$ is first calculated by normalising $SX_b$. In one embodiment, this involves calculating the complex magnitude of the spectrogram $SX_b$ after which the mean of each column is determined which is then used to scale the values in each of the columns of $SX_b$. In another example, a low pass filter such with an auto-regressive filter may be applied to the values.

Once $\mu X_b$ has been determined, then the spectral content difference D(k) may be determined as follows:

$$D(k) = \frac{\mu X_b(k)}{|X_p(k)|}X_p(k) \qquad \text{Equation 5}$$

Referring back to FIG. 12, once the spectral content difference has been determined at step 2530, at step 2540 of FIG. 12 this determined spectral content difference is then removed from the first time window of acoustic signal data to generate the corresponding background benchmarked first time window of acoustic signal data 2550.

Figures 14, 15:
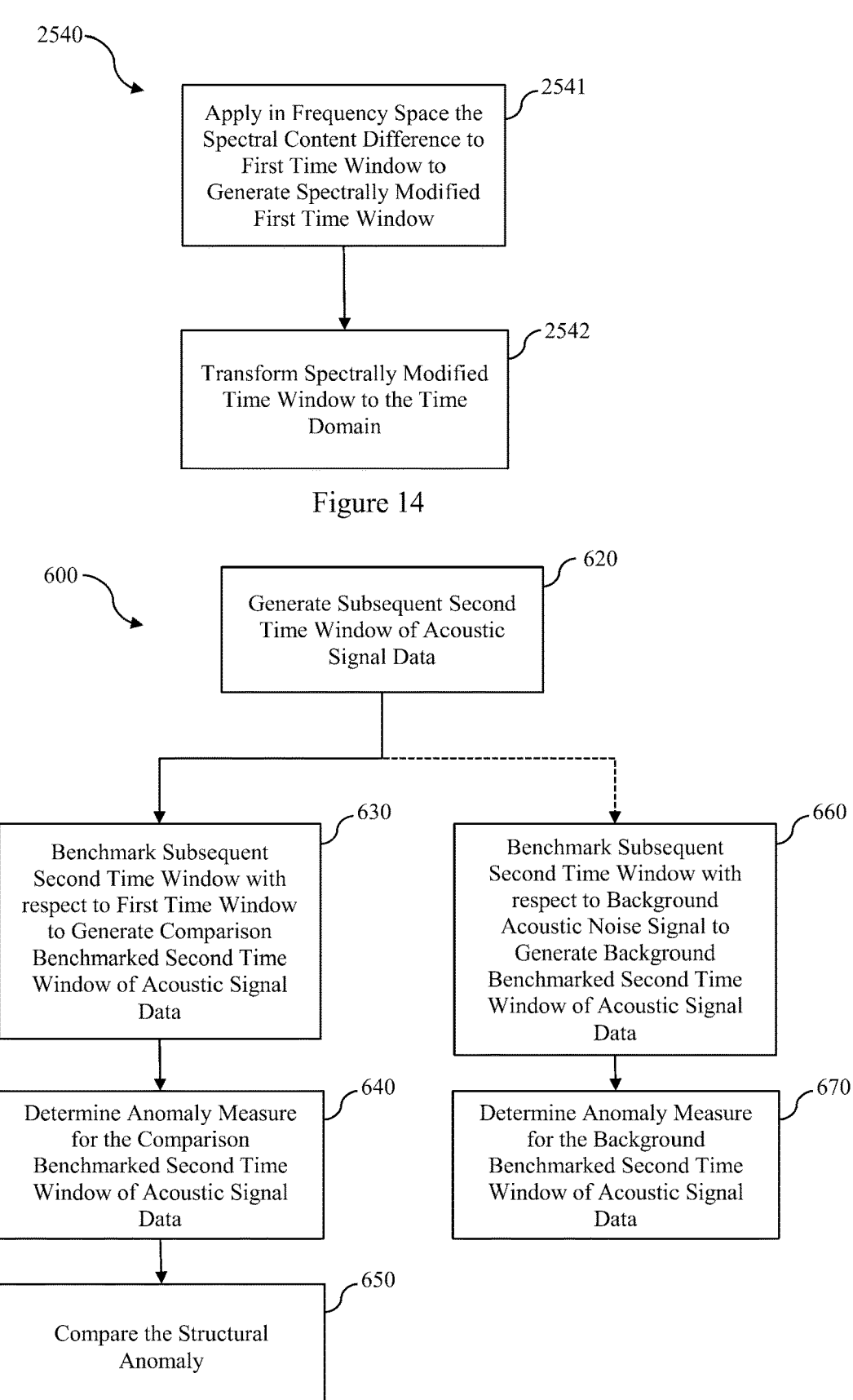
FIG. 14 is a flowchart of a method for removing the spectral content difference from the first time window of acoustic signal data in accordance with an illustrative embodiment.
FIG. 15 is a flowchart of a method for further processing of acoustic signal data in accordance with an illustrative embodiment.

Referring now to FIG. 14, there is shown an example method 2540 for removing the spectral content difference from the first time window of acoustic signal data corresponding to step 2540 of FIG. 12 according to an illustrative embodiment.

At step 2541, the spectral content difference D (k) is applied in the frequency space to the spectral content of the first time window of acoustic signal data to generate a spectrally modified first time window $X_s(k)$ as follows:

$$X_s(k) = \max(X_p(k) - D(k), 0) \qquad \text{Equation 6}$$

As the removal of spectral energy from $X_p(k)$ cannot result in energy levels that drop below 0 the "max" function is used to set an effective floor for $X_s(k)$.

At step 2542, the spectrally modified first time window is transformed to the time domain to generate the background benchmarked first time window of acoustic signal data, ie $x_s$. In one example, the inverse discrete Fourier Transform is applied to each column in the $X_s(k)$ to reconstruct in the time domain the background benchmarked first time window, $x_s$, as follows by adopting the windowing used previously:

$$x_s(n) = \frac{1}{M}\sum_{k=1}^{M-1} X_s(k)e^{i\frac{2\pi n}{M}k} \text{ where } n = 1, \ldots, M \qquad \text{Equation 7}$$

Referring back to FIG. 2, at step 240, following generation of the background benchmarked acoustic signal data, an anomaly measure is determined where the anomaly measure is indicative of a structural anomaly in the pipeline supply network.

In one example, the anomaly measure involves determining a noise measure for the background benchmarked first time window acoustic signal data and then determining whether this noise measure is different to a noise measure of the historical background acoustic signal data.

In the discussion below, the term "noise measure", z, when considered in the context of a time window of acoustic signal data is a statistical measure that corresponds to the degree of variability in the time dependent signal comprising the acoustic signal data and includes, but is not limited to, RMS noise, crest factor, kurtosis, band limited measurements relating to the spectral content of the acoustic signal data, L10 and L90 values, or persistence in time.

In one embodiment, the anomaly measure is taken to indicate the presence of a structural anomaly if the noise measure of the background benchmarked time window of acoustic signal data is identified as being outside of a predetermined band. In this example, the outlier region (OR), which is the area beyond the band, is defined as:

$$OR(\lambda) = \{z : z > Q_3 + \lambda IQR\} \qquad \text{Equation 8}$$

where $Q_3$ and IQR are the $75^{th}$ percentile and interquartile range of in one example the historical background acoustic signal data or other selected historical acoustic signal data. The percentile and IQR in this example are chosen to define the band as they are more robust than mean and the standard deviation. In one example, the background acoustic signal is compiled from the same time window as the first time window for the previous 30 days.

In this example, $\lambda$ is a multiplier which controls the area of outlier region. In this case, $\lambda$ is a user-defined parameter which may be varied depending on the type of structural anomaly.

It is instructive here to review the multiple time scales that are of relevance to the detecting a structural anomaly for the case of a utility scale pipeline supply network for water.

The variation in acoustic signal data associated with a structural anomaly such as a leak is at frequencies typically in the range 1-10 kHz, ie individual pressure oscillations are in the order of milliseconds.

The variation in acoustic signal data associated with the transient environmental noise typically ranges from seconds to minutes.

The time windows of acoustic signal data required for processing in accordance with the present disclosure will have a duration ranging from seconds to hours.

The variation in acoustic signal data associated with diurnal patterns will naturally occur over the time period of a day.

A structural anomaly such as a leak may, once established, be stable for a period of hours, days or months.

As would be appreciated, important objectives of a method for detecting structural anomalies in pipeline supply network include that a leak related anomaly is detected as early as possible and further to minimise the number of false detections. These objectives can demand contradictory parameter settings. For the purpose of early detection, it is preferable to use a short length of the time window and a low threshold value. However, these parameter settings can result in a large number of false alarms at the same time.

In one example, directed to a utility scale pipeline network for delivering water involving cast iron pipes, in order to achieve a balance between the rapidity of detection and the number of false alarms, two different settings are used for different types of structural anomalies. Where the anomaly is a developing circumferential or longitudinal crack, it is expected that the signal will increase and be sustained for a few days or even a few months before there is a burst of the pipe and as such the response time is less critical.

In one non-limiting example, a time window of L=24 hours may be used for this type of structural anomaly. Lower threshold values are used to increase the detectability. Given the longer time window and resultant less noise measures, the number of false alarms is limited even if lower threshold values are used. For a structural anomaly corresponding to a fast developing pipe crack such as a corrosion patch blowout it may only take only a few minutes or hours from the first noticeable increase in the signal to the occurrence of the pipe burst incident. Accordingly, for this type of structural anomaly the detection needs to be as quick as possible so that the maintenance team has a chance to repair before pipe bursts. As a result, a relatively short time window is used and the threshold for detection of a structural anomaly is set to be high to account for the fast and significant changes introduced by the fast developing incidents. In addition, a high threshold is helpful to reduce the number of false alarms.

In one example, a parameters setting of (L=24, $\lambda$=1.5) is used for detection of developing cracks and a parameter setting of (L=1, $\lambda$=15) is used for detection of fast developing blowout incidents.

In another embodiment, the anomaly measure is taken to indicate the presence of a structural anomaly if the cumulative sum of the difference between the noise measure of the background benchmarked or comparison benchmarked time window of acoustic signal data (see below) and a reference value is above a predetermined threshold.

Define the CUSUM $$C_i^+$$

to be the cumulative differences between the noise measure of the time window of the background benchmarked or comparison benchmarked acoustic signal data and the reference value as follows:

$$C_i^+ = \max[0, C_{i-1}^+ + z_i - K] \qquad \text{Equation 9}$$

where $z_i$ is the respective noise measure, and K is the reference value, so that $z_i - K$ is the deviation from the reference value. The choice of $T_1$ is based on the magnitude of the change in noise measure introduced by a structural anomaly.

In this example, when $$C_i^+$$

is greater than a user-defined threshold $T_1$, then the anomaly measure indicates the presence of a structural anomaly.

Considering the example of utility scale pipeline network involving cast iron pipes as referred to above, a parameter setting (L=24, $T_1$=1) is used for detection of developing cracks, and another setting (L=1, $T_1$=10) is used for detection of fast developing blowout incidents. As would be appreciated, the elevation in the noise measure can only be detected if the magnitude is greater than threshold values. A greater threshold value may result in a pipe crack event remaining undetected while smaller threshold values may result in a greater false alarm rate.

In yet another embodiment, the anomaly measure is taken to indicate the presence of a structural anomaly if the background benchmarked or comparison benchmarked time window of acoustic signal data exceeds the Kalman filter estimation of the expected signal by a predetermined threshold.

Kalman filtering provides a complete statistical characterisation of the current state of knowledge of a dynamic system, including the influence of all past measurements. In one example, Kalman filtering is employed to determine an estimate or prediction for the noise measure of the background benchmarked or comparison benchmarked time window of acoustic signal data and the determination of the presence of a structural anomaly, such as a developing pipe crack, can be determined if the noise measure is greater than Kalman filter estimation by a predetermined threshold.

Adopting the Kalman filtering approach, the current state X(k) of the system is computed using the state equation $$X(k) = X(k-1) + Q \qquad \text{Equation 10}$$

Where X(k–1) is the previous state, Q is a random variable representing the process noise. This state equation assumes that the current state is equal to the previous state. In one embodiment, the previous state is determined based on the same time window but for the previous day recognising that many aspects of the background acoustic signal will occur at the same time of day, ie, have a period of 24 hours, eg, the signal is low in the early morning and late night and high during working hours. As an example, it is reasonable to assume that the noise measure between 0:00 am to 1:00 am today should be very similar to the noise measure between 0:00 am to 1:00 am yesterday, if all other conditions remain unchanged.

The measurement of noise Z with a Gaussian measurement noise R can be modelled by $$Z(k) = X(k) + R \qquad \text{Equation 11}$$

Kalman filtering is conceptualised as two phases: a prediction and an update phase. The prediction phase uses the state estimate at the previous time step to produce an estimate at the current time step. The update phase updates and refines the state estimate using current observation information.

Predict Phase 1. Predict State Estimate $$X(k|k-1) = X(k-1|k-1) \qquad \text{Equation 12}$$

Predict Phase 2. Predict Error Covariance $$p(k|k-1) = p(k-1|k-1) + q(k) \qquad \text{Equation 13}$$

where q(k) is the covariance of Q.
Update phase 1. Calculate Kalman Gain $$g(k) = \frac{p(k \mid k-1)}{p(k \mid k-1) + r(k)} \qquad \text{Equation 14}$$

where r(k) is the covariance of R.
Update Phase 2. Update State Estimation $$X(k|k) = X(k|k-1) + g(k)[Z(k) - X(k|k-1)] \qquad \text{Equation 15}$$

Update Phase 3. Update Parameter Covariance $$p(k|k) = [1 - g(k)]p(k|k-1) \qquad \text{Equation 16}$$

In this example, when z–X(k|k) is greater than a user-defined threshold $T_2$, then the anomaly measure indicates the presence of a structural anomaly. The choice of $T_2$ is based on the magnitude of the change in noise measure introduced by a structural anomaly.

In this example, parameter setting (L=24, $T_2$=1) is used for detection of developing cracks, and another setting (L=1, $T_2$=10) is used for detection of fast developing blowout incidents.

Other types of anomaly measures may be employed in accordance with the detection method and system of the present disclosure including those disclosed in Australian Provisional Application No 2019901401 titled "DETECTION OF STRUCTURAL ANOMALIES IN A PIPELINE NETWORK", filed in the name of the present Applicants on 24 Apr. 2019 and which is incorporated by reference in its entirety in this disclosure.

Referring now to FIG. 15, there is shown a flowchart of a method 600 for further processing of acoustic signal data according to an illustrative embodiment. In this example, the presence of a structural anomaly has been detected in the background benchmarked first time window of acoustic signal data.

At step 620 a subsequent second time window of acoustic signal data is generated based on acoustic signal data measured after the acoustic signal data that the first time window of acoustic signal data is based on. In one example, the second time window corresponds to acoustic signal data that is measured immediately after the acoustic signal data forming the basis for the first time window. In another embodiment, the second time window corresponds to acoustic signal data that is measured after a predetermined time interval after the time corresponding to the first time window that is selected based on the type of structural anomaly that is detected and whether that structural anomaly is expected to develop quickly or over an extended period.

As discussed with respect to FIGS. 5 and 6, the generation of the second time window of acoustic signal data may include removing a coherent signal that is present in both the fluid-borne and synchronised environmental acoustic signal data as measured by water and and/or ground acoustic sensors from the fluid-borne acoustic signal data in order to generate the second time window. Similarly, and as discussed with respect to FIGS. 10 and 11, the generation of the second time window may include reinforcing a coherent acoustic signal present in both the fluid-borne and synchronised additional fluid-borne acoustic signal data in the fluid-borne acoustic signal data.

At step 630, the subsequent second time window of acoustic signal data is benchmarked with respect to the first time window of acoustic signal data to determine a corresponding "comparison benchmarked" second time window of noise reduced acoustic signal data. In this specification, the term "comparison benchmarked" signifies that the associated acoustic signal data has been benchmarked in comparison to a selected earlier time window of acoustic signal data as compared to the term "background benchmarked" which signifies that the associated acoustic signal data has been benchmarked relative to the acoustic signal data that is indicative of the background behaviour of the pipeline supply network 100. In accordance with the present disclosure, the benchmarking process may be carried out in line with the method described with respect to FIGS. 12 to 14, excepting that in this case the benchmarking is with respect to the first time window of acoustic signal data which takes the place of the background acoustic signal data 2510 as illustrated in FIG. 12.

At step 640, the anomaly measure is then determined for the comparison benchmarked second time window of acoustic signal data and at step 650 the structural anomaly is characterised by comparing the anomaly measure that has been determined for the background benchmarked first time window of acoustic signal data and the comparison benchmarked second time window of acoustic signal data.

As would be appreciated, by benchmarking the second time window of acoustic signal data relative to the first time window of acoustic signal data, the acoustic signal corresponding to the structural anomaly that was detected in the first time window will set a baseline level against which the second time window of acoustic signal data may then be compared to. As a result, a comparison of the anomaly measure that has been determined for the background benchmarked first time window and the comparison benchmarked second time window which has been benchmarked against the first time window will characterise the structural anomaly. In one example, the structural anomaly may be determined to be increasing in effect or remaining unchanged for the time period between when the first and second time windows were respectively generated.

In another embodiment, depicted at steps 660 and 670, the subsequent second time window of acoustic signal data is benchmarked with respect to the background acoustic signal data to generate a background benchmarked second time window of acoustic signal data and the anomaly measure is determined at step 670 based on this background benchmarked second time window of acoustic signal data. This process is similar to steps 230 and 240 referred to in FIG. 2 above incorporating the benchmarking process described with reference to FIGS. 12 to 14.

As can be seen by inspection, the left hand (ie steps 630, 640 and 650) and right hand branches (ie steps 660 and 670) perform different comparison functions. The left branch compares the current acoustic signal (ie, the second time window) to a previously determined acoustic signal (ie, the first time window) as compared to the right branch which compares the current acoustic signal (ie, the second time window) with the background acoustic signal. In this manner, the left hand branch characterises the dynamic behaviour or gradient of the structural anomaly as compared to the right hand branch which signifies the presence or otherwise of the structural anomaly.

This process may then be repeated as required by generating third, fourth, fifth time, windows of acoustic signal data taken at subsequent later times and then processing these with respect to acoustic noise data corresponding to one or more of the previous time windows of acoustic signal data or to the background acoustic noise data as required.

Figure 16:
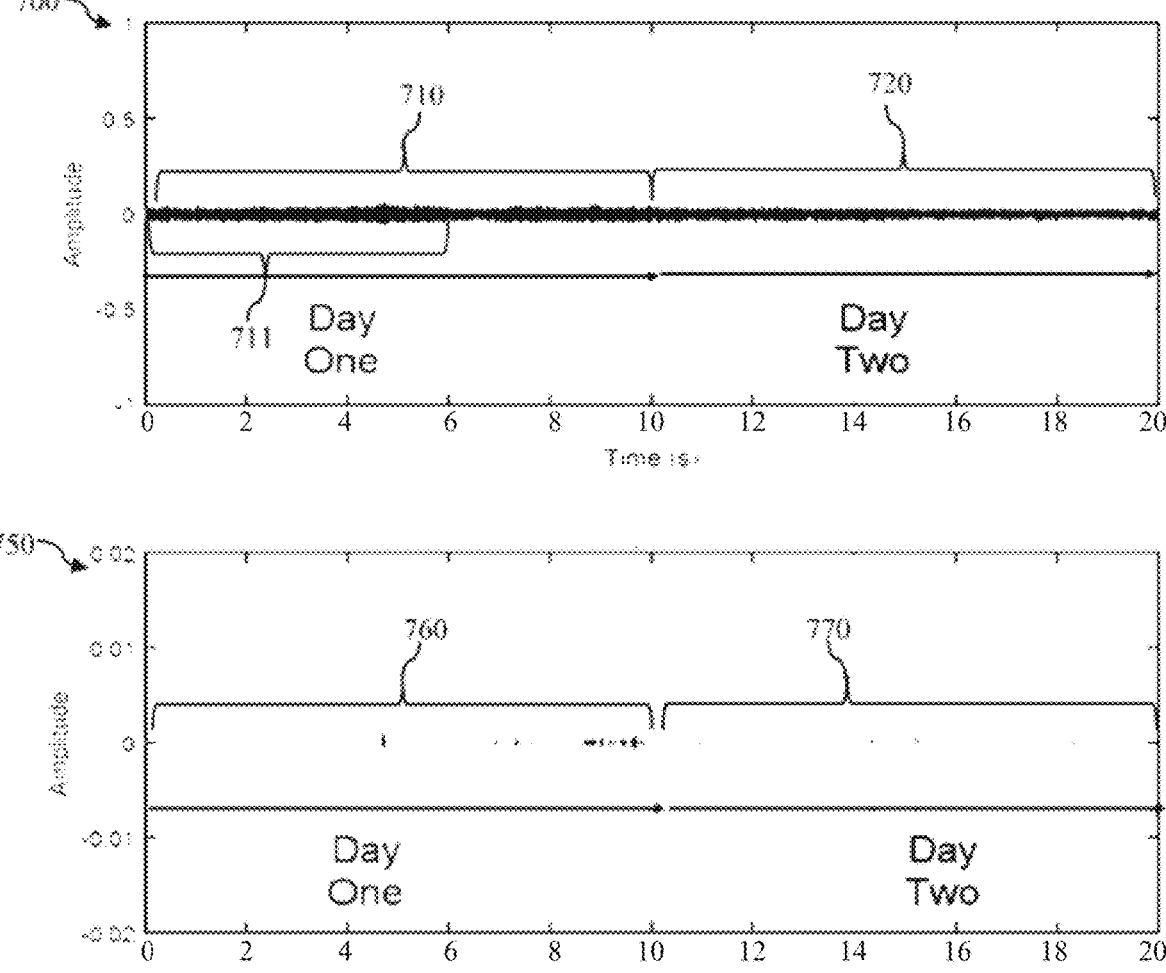
FIG. 16 shows first and second plots of acoustic signal data determined in accordance with an illustrative embodiment.

Referring now to FIG. 16, there are shown first and second plots 700, 750 of acoustic signal data determined according to an illustrative embodiment. First plot 700 shows a time window of background acoustic signal data 710 and a subsequent first time window of acoustic signal data 720. In this example, the time window of background acoustic signal data 710 comprises a 10 second window of acoustic signal data taken from "Day One" and second time window 720 comprises a subsequent 10 second window of acoustic signal data taken from "Day Two" at a corresponding time. In this example, time window 710 is taken to be background acoustic signal data that characterises the background behaviour of pipeline supply network 100 (see step 230 of FIG. 2). In this example, an initial six second window 711 of time window 710 is employed but as would be appreciated, and in accordance with the present disclosure, the background acoustic signal data may be formed of any time window or composition of time windows of acoustic signal data that characterises the pipeline supply network. This includes selecting the "background" time window to correspond to the time window in which measurements are to be taken on an ongoing basis.

Referring now to plot 750, there is shown background benchmarked first time window of acoustic signal data 770 resulting from benchmarking the first time window of acoustic signal data 720 with respect to the background acoustic signal data corresponding to time window 710. In this example, it can be seen from visual inspection that there is no indication of a structural anomaly in the background benchmarked first time window of acoustic signal data 770. Plot 750 also shows reference time window 760 which is the result of the background acoustic signal data 710 being benchmarked with respect to itself. As expected, reference time window 760 shows no indication of a structural anomaly.

Figure 17:
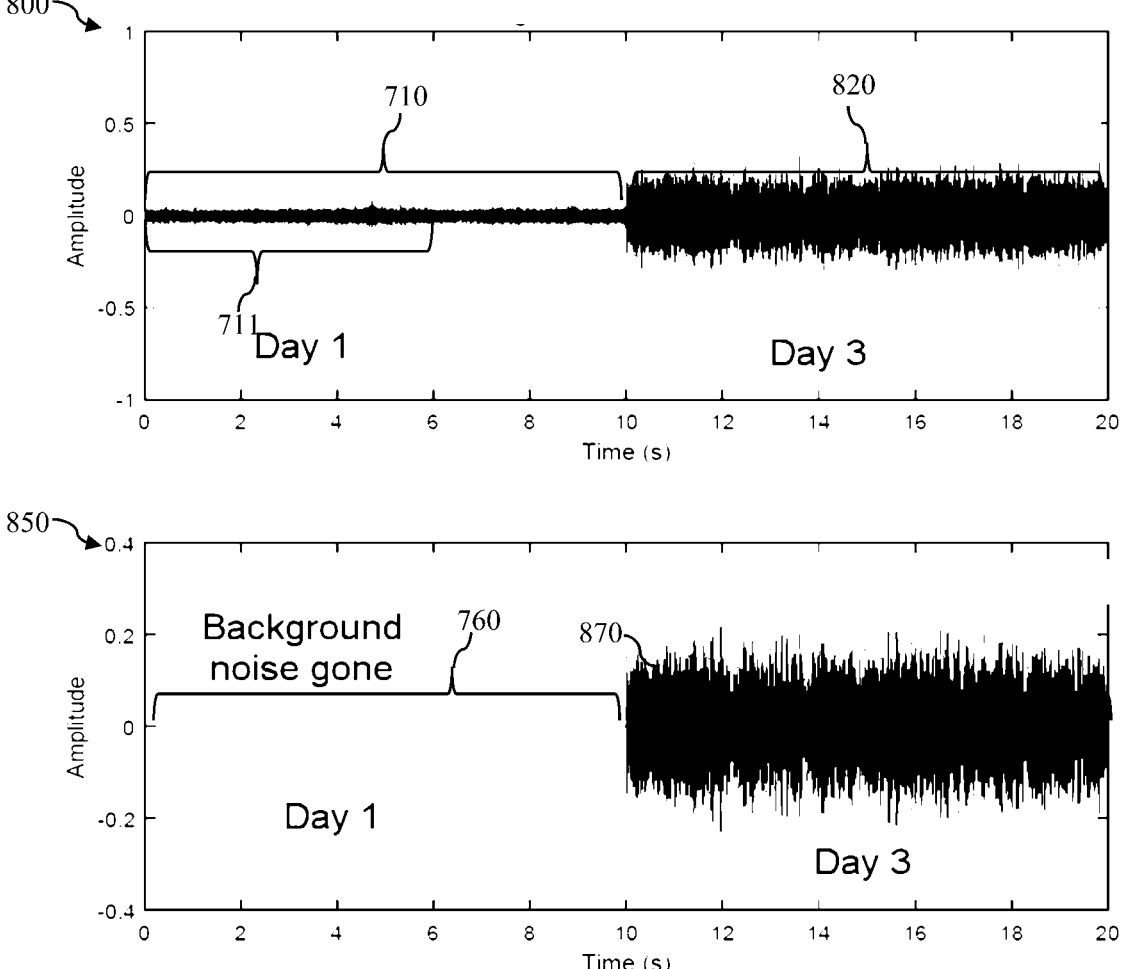
FIG. 17 shows first and second plots of acoustic signal data determined in accordance with an illustrative embodiment.

Referring now to FIG. 17, there are shown first and second plots 800, 850 of acoustic signal data determined according to an illustrative embodiment. First plot 800 shows the time window of background acoustic signal data 710 depicted in FIG. 16 and a subsequent second time window of acoustic signal data 820. As with FIG. 16, in this example, the time window of background acoustic signal data 710 comprises a 10 second window of acoustic signal data taken from "Day One". Second time window 820 comprises a subsequent 10 second window of acoustic signal data taken from in this example "Day Three" at a corresponding time. Time window 710 is once again taken to be background acoustic signal data that characterises the background behaviour of pipeline supply network 100 (see step 230 of FIG. 2).

Referring now to plot 850, there is shown a background benchmarked second time window of acoustic signal data 870 resulting from benchmarking the second time window of acoustic signal data 820 with respect to the background acoustic signal data corresponding to time window 710. In this example, it can be seen from visual inspection, and by comparison with "Day 2" (eg, see acoustic signal data 770 in FIG. 16) that there is now an indication of a structural anomaly (ie, a crack/leak in this example) in the form of a high frequency signal in the background benchmarked second time window of acoustic signal data 870 corresponding to the second time window 820. As with plot 750, plot 850 also shows time window 760 which is the result of the background acoustic signal data 710 being benchmarked with respect to itself.

Figure 18:
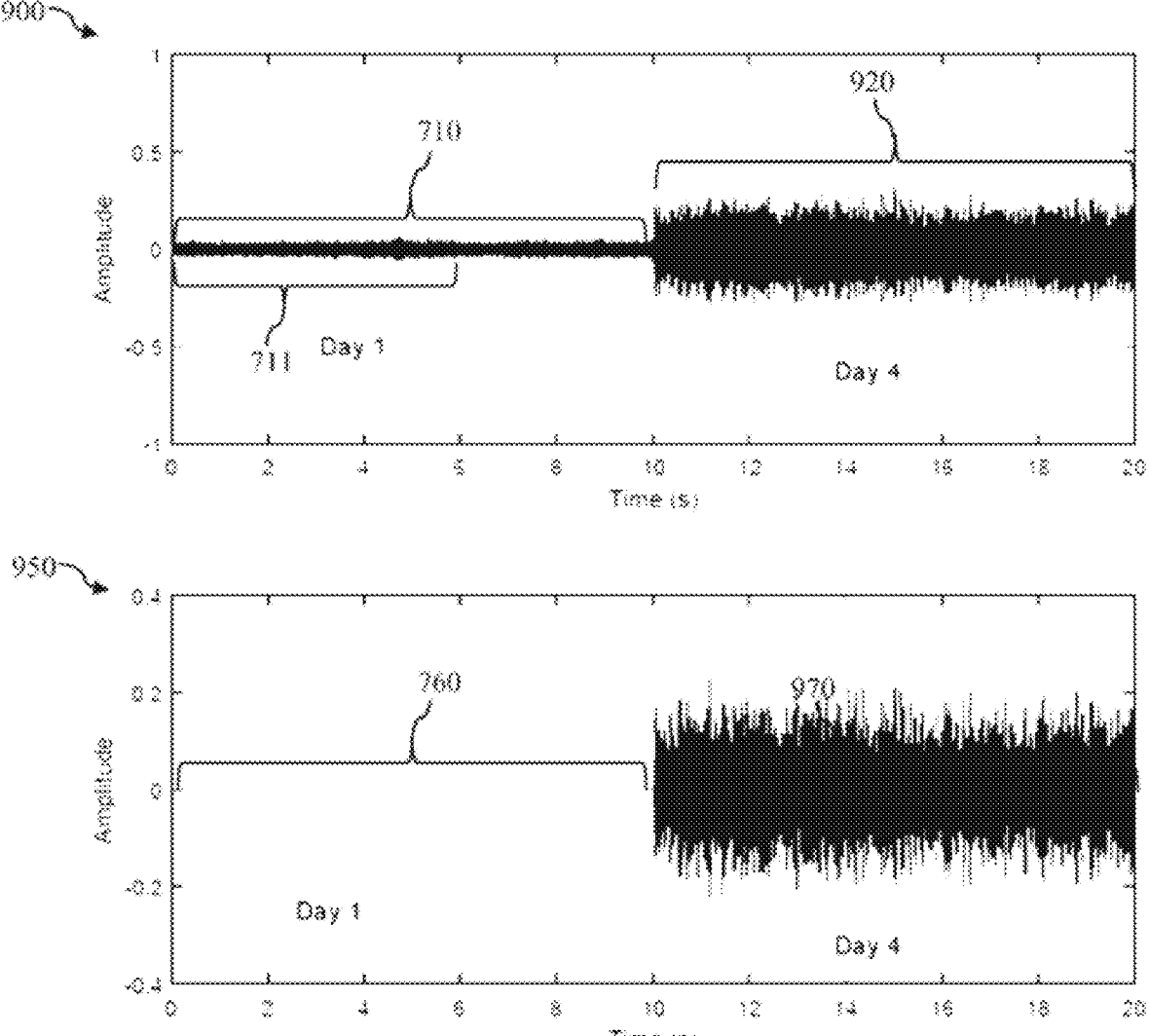
FIG. 18 shows first and second plots of acoustic signal data determined in accordance with an illustrative embodiment.

Referring now to FIG. 18, there are shown first and second plots 900, 950 of acoustic signal data determined according to an illustrative embodiment. First plot 900 shows the time window of background acoustic signal data 710 depicted in FIG. 16 and a subsequent third time window of acoustic signal data 920. As with FIG. 16, in this example, the time window of background acoustic signal data 710 comprises a 10 second window of acoustic signal data taken from "Day One". Third time window 920 comprises a subsequent 10 second window of acoustic signal data taken from in this example "Day Four". Time window 710 is once again taken to be background acoustic signal data that characterises the background behaviour of pipeline supply network 100 (see step 230 of FIG. 2).

Referring now to plot 950, there is shown a background benchmarked third time window of acoustic signal data 970 resulting from benchmarking the third time window of acoustic signal data 920 with respect to the background acoustic signal data corresponding to time window 710. Once again, it can be seen from visual inspection of the background benchmarked third time window of acoustic signal data 970 corresponding to the third time window 920 that the structural anomaly identified for "Day 3" is still present. As with plot 750, plot 950 also shows time window 760 which is the result of the background acoustic signal data 710 being processed with respect to itself.

As can be seen from inspection, the scenarios depicted in FIGS. 16, 17 and 18 correspond to the right hand branch of FIG. 15 as discussed above where the respective time windows of acoustic signal data are compared to baseline or background acoustic signal data that characterises the pipeline supply network.

Figure 19:
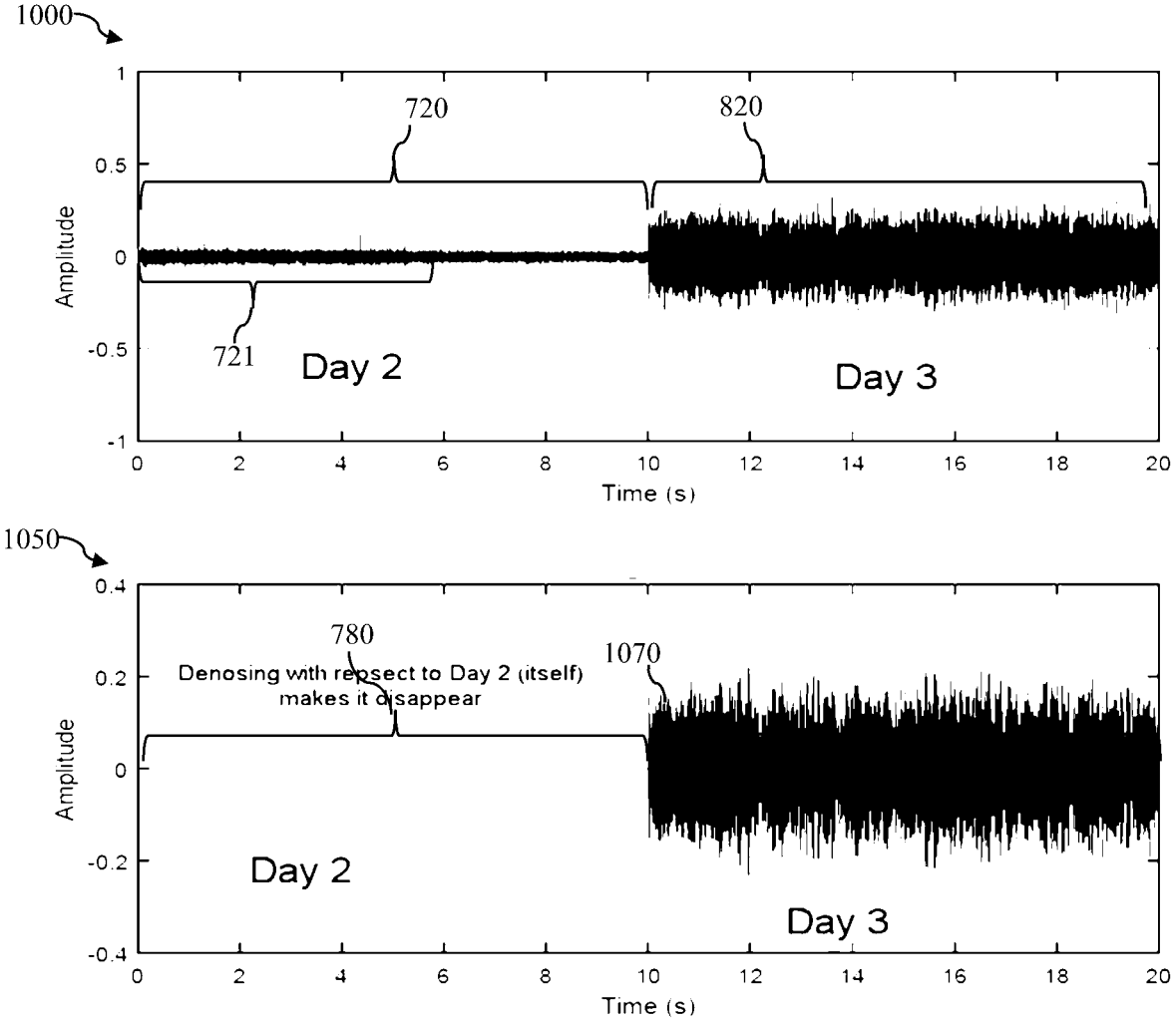
FIG. 19 shows first and second plots of acoustic signal data determined in accordance with an illustrative embodiment.

Referring now to FIG. 19, there are shown first and second plots 1000, 1050 of acoustic signal data determined according to an illustrative embodiment. First plot 1000 shows the first time window of acoustic signal data 720 depicted in FIG. 16 corresponding to "Day 2" and a subsequent second time window of acoustic signal data 820 corresponding to "Day 3" as depicted in FIG. 17. As with FIG. 16, the first time window of background acoustic signal data 720 comprises a 10 second window of acoustic signal data taken from "Day Two" and the second time window 820 comprises a subsequent 10 second window of acoustic signal data taken from in this example "Day Three".

Referring now to plot 1050, there is shown a comparison benchmarked second time window acoustic signal data 1070 resulting from benchmarking in this case the second time window of acoustic signal data 820 with respect to first time window of acoustic signal data 720 (see step 630 of FIG. 15). This may be contrasted with the approach shown in FIG. 17 where the benchmarking is with respect to the background acoustic signal data which in this case corresponded to "Day 1". In this case, because there was no structural anomaly in the first time window 720 corresponding to "Day 2" and the structural anomaly is present in the second time window 820 corresponding to "Day 3", the difference between the de-noised "Day 2" 780 (ie, result of the first time window 720 being benchmarked with respect to itself) and the corresponding comparison benchmarked second time window 1070 indicates the formation of a structural anomaly.

Figure 20:
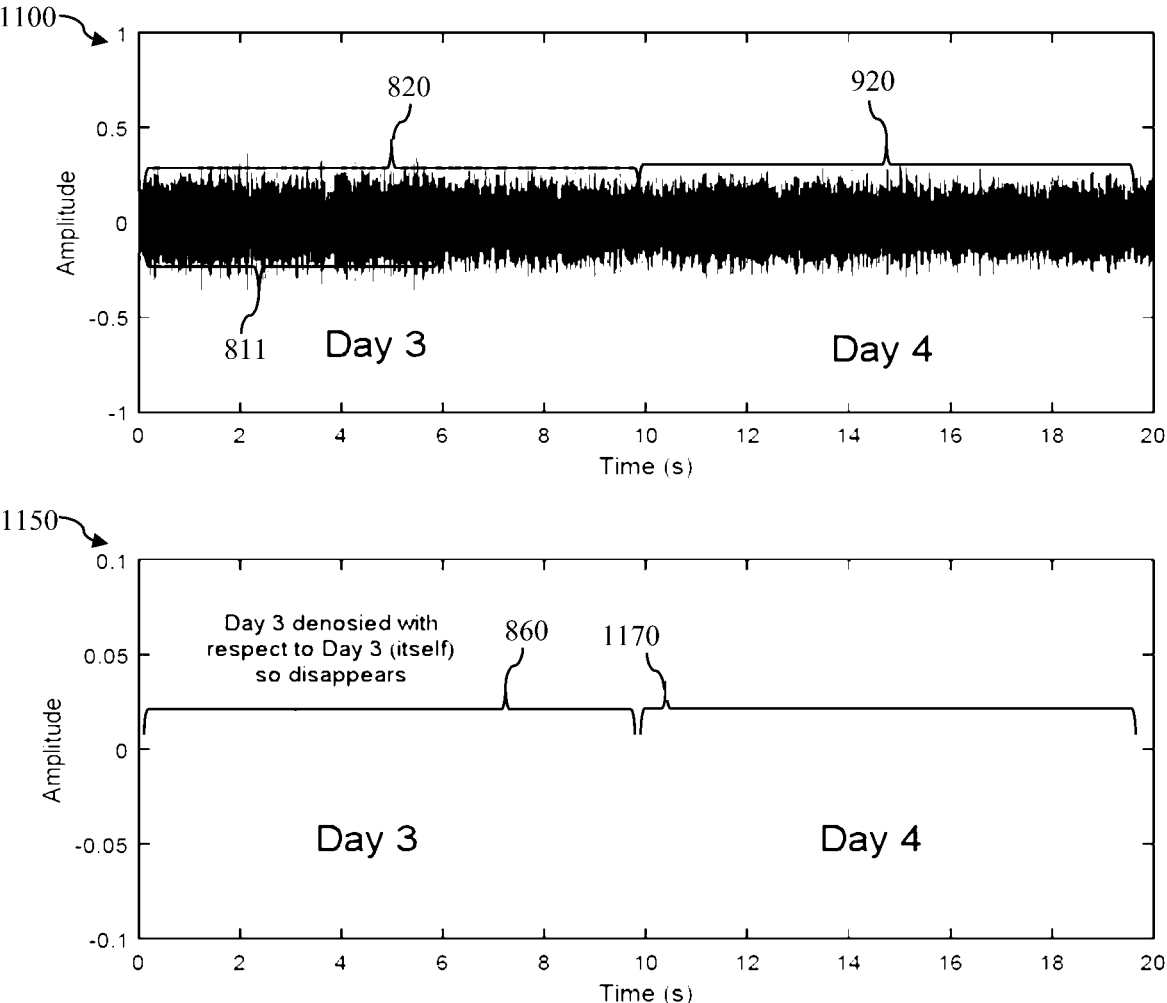
FIG. 20 shows first and second plots of acoustic signal data determined in accordance with an illustrative embodiment.

Referring now to FIG. 20, there are shown first and second plots 1100, 1150 of acoustic signal data determined according to an illustrative embodiment. First plot 1100 shows the second time window of acoustic signal data 820 first depicted in FIG. 17 and also in FIG. 19 corresponding to "Day 3" and a subsequent third time window of acoustic signal data 920 corresponding to "Day 4" as depicted in FIG. 18.

Referring now to plot 1150, there is shown a comparison benchmarked third time window of noise of acoustic signal data 1170 resulting from benchmarking in this case the third time window of acoustic signal data 920 with respect to the second time window of acoustic noise data 820. Again, this may be contrasted with the approach shown in FIG. 18 where the de-noising is with respect to the background acoustic noise data which in this case corresponded to "Day 1". In this case, the third comparison benchmarked third time window 1170 shows virtually no signal signifying that the structural anomaly is still present but that it has not increased, ie the structural anomaly identified at "Day 3" is still present at "Day 4". Plot 1150 also shows time window 860 which is the result of the second time window 820 being processed with respect to its own noise data. In the case where the comparison benchmarked third time window of acoustic data 1170 does show the presence of a signal then this will indicate that there has been a further development in the structural anomaly between in this case "Day 3" and "Day 4".

As can be seen from inspection, the scenarios depicted in FIGS. 19 and 20 correspond to the left hand branch of FIG. 15 as discussed above where the respective time windows of acoustic signal data are compared to preceding time windows of acoustic signal data in order to show the time development or gradient of the structural anomaly over the time.

While the above examples have been described by reference to visual inspection of the plots in FIGS. 16 to 20, it would be appreciated that relevant anomaly measures would be determined for the respective time windows of noise reduced acoustic signal data in accordance with the present disclosure and relevantly compared in order to characterise the structural anomaly.

Referring once to FIG. 2, in the scenario at step 240 when it is determined that the first time window of background noise reduced acoustic signal data does not include the presence of a structural anomaly then in another embodiment the background acoustic signal data may be supplemented with the first time window of acoustic signal data to further characterise the pipeline supply network 100.

Methods and systems for detecting a structural anomaly in a pipeline supply network implemented in accordance with the present disclosure provide a number of substantive benefits over previous techniques. It is often a feature of the structural anomalies that the associated acoustic signal will present similarly to general background acoustic "noise" of the pipeline supply network. One example is a through-wall crack induced discharge whose acoustic signal is typically small compared to the ambient background acoustic benchmark noise.

In this case, any visual inspection of a trace of the acoustic signal data or listening to the sensor noise will be unable to discern the small changes in magnitude or frequency caused by a structural anomaly such as discharge through a pipe crack. By being able to benchmark the acoustic signal data against the historical background acoustic data associated with the pipeline supply network, this will substantially reduce the background noise component from the acoustic signal data and as a result increase the ability of the present method and system to detect the present of a structural anomaly by calculation of suitable anomaly measures.

Furthermore, as exemplified in one embodiment of the present disclosure, by respectively benchmarking signals against each other over successive time periods, the gradient of a signal corresponding to a structural anomaly may be characterised and analysed as small changes can be discerned in the signal without being swamped by the presence of the structural anomaly.

In addition, embodiments of the present disclosure provide methods for enhancing water-borne acoustic signal data prior to any benchmarking process by either removing signals that are both present in water-borne acoustic signal data and associated environmental acoustic signal data or by reinforcing together separate measurements of the water-borne acoustic signal. This can allow acoustic signal measurements to be taken at times where otherwise the ambient acoustic noise would overwhelm any signal associated with a structural anomaly.

Those of skill in the art would appreciate that the various illustrative logical blocks, modules, circuits, and algorithm steps described in connection with the embodiments disclosed may be implemented as electronic hardware, computer software or instructions, or combinations of both. To clearly illustrate this interchangeability of hardware and software, various illustrative components, blocks, modules, circuits, and steps have been described above generally in terms of their functionality. Whether the disclosed functionality is implemented as hardware or software will depend upon the requirements of the application and design constraints imposed on the overall detection system. As an example, data processor 320 may encompass one or more separate applications on a single digital computer or processor or be distributed over a number of digital computers or processors depending on requirements.

As a further example, a measurement station may comprise a selection of one or more of the following types of sensors:

acoustic sensors immersed in the fluid or mounted on the pipe wall or attached fittings (eg, valves) and functioning as internal or external fluid acoustic sensors for measuring directly or indirectly fluid-borne vibro-acoustic energy;

accelerometers mounted or connected to the pipe wall or attached fittings (eg, valve) functioning as external fluid acoustic sensors for indirectly measuring fluid-borne vibro-acoustic energy;

hydrophones immersed in the fluid for directly measuring fluid-borne vibro-acoustic energy;

pressure transducers immersed in the fluid for directly measuring fluid-borne vibro-acoustic energy in the form of pressure waves in the fluid;

microphones for measuring air-borne vibro-acoustic energy around the pipe and/or any attached fittings; or accelerometers or seismic sensors for measuring ground borne vibro-acoustic energy located in the ground surrounding the pipe.

In another example, respective sensors may be oriented in different directions in order to determine directional information to assist in determining a source location for the measured vibro-acoustic energy. In one example, acoustic sensors may be connected to the wall of a pipe in three different directions to provide directional information to locate a source of vibro-acoustic energy corresponding to a leak in the pipeline supply network.

As would be appreciated, the use of terms such as fluid-borne, ground-borne or air-borne as used throughout the specification indicate that the respective sensor is configured to measure predominantly fluid-borne, ground-borne or air-borne vibro-acoustic energy respectively. It is the nature of these vibro-acoustic systems that the components of the system will be coupled in an acoustic sense and, as an example, a sensor configured to measure fluid-borne vibro-acoustic energy will also sense other forms of vibro-acoustic energy transmitted through the ground, air, pipe wall and the like.

In one example, the DAQ module may comprise a NI CRIO 9040 DAQ processor/controller configured to receive one or more NI 9232 voltage input cards for acquiring the output from the various sensors and also to receive a NI 9237 4 channel bridge module to receive the outputs from acoustic sensors in the form of pressure transducers.

Each of the acoustic signal outputs from the sensors may be sampled at different rate. Exemplary sampling rate ranges include, but are not limited to, greater than 0 kHz and less than 1 kHz, 1 kHz-2 kHz, 2 kHz-3 kHz, 3 kHz-4 kHz, 4 kHz-5 kHz, 5 kHz-6 kHz, 6 kHz-7 kHz, 7 kHz-8 kHz, 8 kHz-9 kHz, 9 kHz-10 kHz, or greater than 10 kHz. In another example embodiment, the acoustic signal outputs of one or more of the sensors may be sampled synchronously, ie, at the same frequency.

In this example, the DAQ module may be configured so that acoustic signal data may be transmitted from the sensors (and DAQ module) and control requests (automated or otherwise) may be sent to the DAQ module (eg, to adjust data type sampling rates).

In one example, the acoustic signal data received from the various acoustic sensors is synchronised in time to an accuracy of approximately 1 microsecond or better.

As discussed above, in one example the synchronisation of acoustic signal data may be achieved by a centralised GPS module forming part of the DAQ module that applies a synchronised time stamp to each of the incoming data streams from the respective acoustic sensors. In another example, one or more of the acoustic sensor may themselves include a local GPS module to provide this synchronisation capability, ie to synchronise any sensor based on-board clocks to the GPS signal. In one example, the on-board clocks may be aligned with the GPS PPS 1 Hz signal that is accurate to within 90 nano-seconds of the high resolution clocks on the relevant GPS satellites. In one example, the DAQ module may update the timing every second while in GPS synchronised mode. As would be appreciated, this time may be lengthened depending on the accuracy of the internal DAQ module or sensor clocks.

As would be appreciated, other synchronisation arrangements not necessarily involving GPS systems may be adopted (ie, synchronisation in the order of 1 micro-second).

In another example, the synchronisation of acoustic signal data that has been simultaneously measured from different sensors may be achieved using suitable signal processing techniques in either the frequency or time domain in which case the time synchronisation of the sensors need only be in the 100s of micro-seconds.

In one example embodiment, the acoustic sensors may be distributed over an extended distance and in this case the relevant acoustic signal data would be timing compensated based on the distance of the sensor from the measurement station to allow relevant correlations and coherence between the signal to be exploited as described above with respect to FIGS. 5-11 to produce enhanced signals that may be distinguished from the background noise.

The acoustic signal data may be stored locally at the DAQ module and/or transmitted from the DAQ to a cloud or other remote storage by any suitable communications means. In one example, the transmission of data (and receipt of new control instructions) is achieved via a mobile GSM communications module incorporated into the DAQ module.

In one example, the DAQ module is configured to generate and transmit summary statistical information for each sensor at a selectable rate for each acoustic sensor (eg, 10 minutes). For the accelerometers, hydrophones and microphones these statistics may include, but are not limited to:

root mean square (RMS) magnitude;
change in RMS;
median frequency level;
current frequency/spectral levels (magnitudes);
peak magnitude; or
entropy measures.

For the pressure transducers the statistics may include, but are not limited to:

any selection of the values listed in relation to the sensors above; and/or mean pressure;

maximum pressure;

minimum pressure; or pressure flux level (sustained band size).

In addition to the summary statistical information, acoustic and pressure magnitude data (eg, RMS values) may be continuously transmitted for all sensors (accelerometers, hydrophones, microphones and pressure transducers) at a selectable (and adjustable) rate. In various non-limiting examples, the summary statistical information may be updated every minute, every 10 minutes, hourly or daily. In other examples, different subsets of the summary statistical information may be updated at different rates dependent on requirements. As would be appreciated, these update rates may be varied by the use of suitable control signals sent to the sensor or DAQ module.

The statistical and continuous acoustic magnitude data will be subject to anomaly detection and characterisation analysis in accordance with the present disclosure. Some of this change and fault detection may be undertaken locally at the DAQ module before data transmission. In one example, on detection of an anomaly the DAQ module may adjust the type and rate of data collection occurs such that additional data is rapidly transmitted to remote cloud and/or remote premises servers where more extensive processing occurs to characterise the structural anomaly.

In one example, following the detection of a structural anomaly, commands may be sent remotely to the DAQ module to change the type and rate of data collection and then store and transmit this additional data for analysis. In one non-limiting example, following the detection of a structural anomaly, the length and rate of sound file measurement might be increased from 10 seconds once per day to 30 seconds every 30 minutes based on a change (increase) in the continuously measured and transmitted acoustic signal data for a given location.

In one example, where the DAQ module is based on a National Instruments™ architecture, the user interface to the DAQ module employs the LabVIEW™ software system.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A method for detecting a structural anomaly in a pipeline supply network, the pipeline supply network configured to supply fluid to multiple receiving locations, comprising:

receiving acoustic signal data from a selected location in the pipeline supply network;

generating a first time window of acoustic signal data based on the acoustic signal data;

benchmarking the first time window of acoustic signal data with respect to historical background acoustic signal data characterising the pipeline supply network to generate a corresponding background benchmarked first time window of acoustic signal data, wherein benchmarking the first time window of acoustic signal data with respect to historical background acoustic signal data characterising the pipeline supply network includes:

determining an estimated spectral content difference between the first time window of acoustic signal data and the historical background acoustic signal data, wherein determining the estimated spectral content difference between the first time window and the background acoustic signal data includes:

determining the spectral content of the historical background acoustic signal data;

determining the spectral content of the first time window of acoustic signal data; and determining in frequency space the difference between the spectral content of the background acoustic signal data and the spectral content of the first time window of acoustic signal data; and removing the spectral content difference from the first time window of acoustic signal data to generate the corresponding background benchmarked first time window of acoustic signal data; and determining an anomaly measure for the background benchmarked first time window of acoustic signal data, wherein the anomaly measure indicates a presence of the structural anomaly, wherein on determining the presence of the structural anomaly in the background benchmarked first time window of acoustic signal data then:

generating a subsequent second time window of acoustic signal data;

benchmarking the subsequent second time window of acoustic signal data with respect to the first time window of acoustic signal data to generate a corresponding comparison benchmarked second time window of acoustic signal data;

determining the anomaly measure for the comparison benchmarked second time window of acoustic signal data; and characterising the structural anomaly by comparing the anomaly measure determined for the background benchmarked first time window of acoustic signal data with the anomaly measure determined for the comparison benchmarked second time window of acoustic signal data, wherein characterising the structural anomaly includes determining whether the structural anomaly is increasing, reducing or remains unchanged for a time period between the first and second time windows.

2. The method of claim 1, wherein removing the spectral content difference from the first time window of acoustic signal data includes:

applying in frequency space the spectral content difference to the spectral content of the first time window of acoustic signal data to generate a spectrally modified first time window; and transforming the spectrally modified first time window to the time domain to generate the corresponding background benchmarked first time window of acoustic signal data.

3. The method of claim 1, wherein benchmarking the subsequent second time window of acoustic signal data with respect to the first time window of acoustic signal data includes:

determining the spectral content difference between the second time window of acoustic signal data and the first time window of acoustic signal data; and removing the spectral content difference from the second time window of acoustic signal data to generate the corresponding comparison benchmarked second time window of acoustic signal data.

4. The method of claim 3, wherein determining the spectral content difference between the second time window and the first time window includes:

determining the spectral content of the first time window of acoustic signal data;

determining the spectral content of the second time window of acoustic signal data; and determining in frequency space the difference between the spectral content of the first time window of acoustic signal data and the spectral content of the second time window of acoustic signal data.

5. The method of claim 4, wherein removing the spectral content difference from the second time window of acoustic signal data includes:

applying in frequency space the spectral content difference to the spectral content of the second time window of acoustic signal data to generate a spectrally modified second time window; and transforming the spectrally modified second time window to the time domain to generate the corresponding background benchmarked second time window of acoustic signal data.

6. The method of claim 1, comprising:

benchmarking the second time window of acoustic signal data with respect to background acoustic signal data characterising the pipeline supply network to generate a corresponding background benchmarked second time window of acoustic signal data; and determining the anomaly measure for the background benchmarked second time window of acoustic signal data.

7. The method of claim 1, further comprising on determining that the background benchmarked first time window of acoustic signal data does not indicate the presence of the structural anomaly then supplementing the background acoustic signal data with the first time window of acoustic signal data to further characterise the pipeline supply network.

8. The method of claim 1, wherein measuring acoustic signal data at the selected location includes measuring at the selected location fluid-borne vibro-acoustic energy transferred by fluid moving through the pipeline supply network to generate fluid-borne acoustic signal data.

9. The method of claim 8, wherein generating the first time window of acoustic signal data includes enhancing the fluid-borne acoustic signal data with other simultaneously measured synchronised acoustic signal data.

10. The method of claim 9, wherein enhancing the fluid-borne acoustic signal data with other simultaneously measured synchronised acoustic signal data includes:

simultaneously measuring environmental vibro-acoustic energy proximal to the selected location to generate synchronised environmental acoustic signal data; and processing the fluid-borne acoustic signal data to remove from the fluid-borne acoustic signal data, a coherent acoustic signal present in both the fluid-borne and the synchronised environmental acoustic signal data for the time window.

11. The method of claim 10, wherein processing the fluid-borne acoustic signal to remove the coherent acoustic signal includes adaptively filtering the fluid-borne acoustic signal data with respect to the synchronised environmental acoustic signal data by a LMS filter that seeks to minimise an error between an output signal and a desired signal comprising the fluid-borne acoustic signal data.

12. The method of claim 10, wherein processing the fluid-borne acoustic signal to remove the coherent acoustic signal includes determining a non-coherent output power of the fluid-borne acoustic signal data with respect to synchronised environmental acoustic signal data.

13. The method of claim 10, wherein simultaneously measuring environmental vibro-acoustic energy proximal to the selected location includes simultaneously measuring air-borne vibro-acoustic energy in the space proximal to the selected location to generate synchronised environmental acoustic signal data comprising air-borne acoustic signal data.

14. The method of claim 10, wherein simultaneously measuring environmental vibro-acoustic energy proximal to the selected location includes simultaneously measuring ground-borne vibro-acoustic energy in the ground proximal to the selected location to generate synchronised environmental acoustic signal data comprising ground-borne acoustic signal data.

15. The method of claim 9, wherein enhancing the fluid-borne acoustic signal data with other simultaneously measured acoustic signal data includes:

simultaneously measuring fluid-borne vibro-acoustic energy at a different location to the selected location to generate synchronised additional fluid-borne acoustic signal data; and processing the fluid-borne acoustic signal to reinforce in the fluid-borne acoustic signal data, a coherent acoustic signal present in both the fluid-borne and synchronised additional fluid-borne acoustic signal data for the time window.

16. The method of claim 15, wherein processing the fluid-borne acoustic signal to reinforce a coherent acoustic signal present in both the fluid-borne and synchronised additional fluid-borne acoustic signal data includes adaptively filtering the fluid-borne acoustic signal data with respect to the synchronised additional fluid-borne acoustic signal data by a LMS filter that seeks to minimise an error between an output signal and a desired signal comprising the fluid-borne acoustic signal data.

17. The method of claim 15, wherein processing the fluid-borne acoustic signal to reinforce the coherent acoustic signal includes determining a coherent output power of the fluid-borne acoustic signal data with respect to synchronised additional fluid-borne acoustic signal data.

18. The method of claim 1, wherein the first and second time windows of acoustic data are selected from a time when the corresponding background acoustic noise of the pipeline supply network is below a minimum threshold.

19. The method of claim 1, wherein the first and second time windows of acoustic data are selected from acoustic signal data measured at the same time of day.

20. The method of claim 1, wherein the structural anomaly comprises a leak in the pipeline supply network.

21. The method of claim 20, wherein the pipeline supply network comprises a cast iron pipe, and wherein the structural anomaly includes a circumferential or longitudinal crack in the cast iron pipe.

22. The method of claim 1, further comprising measuring the acoustic signal data at the selected location.

23. A detection system for detecting a structural anomaly in a pipeline supply network, the pipeline supply network configured to supply fluid to multiple receiving locations, comprising:

a sensor network including a plurality of measurement stations for measuring acoustic signal data at plurality of locations in the pipeline supply network;

one or more data processors operatively connected to the sensor network and configured to carry out the method of claim 1.

* * * * *